(12) United States Patent
Conrad et al.

(10) Patent No.: US 10,352,743 B1
(45) Date of Patent: Jul. 16, 2019

(54) FLOW SENSOR BASED ON ELECTRICAL CAPACITY

(71) Applicant: Sensors That Count, LLC., Des Moines, IA (US)

(72) Inventors: Larry M. Conrad, Walker, IA (US); Robert J. Weber, Des Moines, IA (US)

(73) Assignee: SENSORS THAT COUNT, L.L.C., Des Moines, IA (US)

( * ) Notice: Subject to any disclaimer, the term of this patent is extended or adjusted under 35 U.S.C. 154(b) by 0 days.

(21) Appl. No.: 15/822,181

(22) Filed: Nov. 26, 2017

Related U.S. Application Data

(63) Continuation-in-part of application No. 14/037,680, filed on Sep. 26, 2013, now abandoned.

(51) Int. Cl.
*G01D 5/24* (2006.01)
*G01F 1/58* (2006.01)
(Continued)

(52) U.S. Cl.
CPC .......... *G01F 1/64* (2013.01); *G01D 5/2405* (2013.01); *G01F 1/588* (2013.01); *G01F 1/665* (2013.01); *G01F 1/6847* (2013.01); *G01N 22/04* (2013.01); *G01R 27/2635* (2013.01); *G01N 2011/0066* (2013.01)

(58) Field of Classification Search
CPC . G01F 1/64; G01F 1/588; G01F 1/665; G01F 1/6847; G01D 5/2405; G01N 22/04; G01R 27/2635
See application file for complete search history.

(56) References Cited

U.S. PATENT DOCUMENTS 4,211,970 A * 7/1980 Fitzky .................... G01N 22/04
324/634
4,619,146 A * 10/1986 Teodorescu ............... G01F 1/24
73/861.54
(Continued)

OTHER PUBLICATIONS

Shawana Tabassum et al., Patterning of nanophotonic structures at optical fiber tip for refractive index sensing, 2016 IEEE Sensors, Electronic ISBN: 978-1-4799-8287-5, Oct. 30-Nov. 3, 2016, 3 Pages, CFP16SEN-ART.

*Primary Examiner* — Mohamed Charioui
*Assistant Examiner* — Brandon J Becker
(74) *Attorney, Agent, or Firm* — Lawrence N. Ginsberg

(57) ABSTRACT

An electric measurement method and apparatus for detecting a mass by an electric capacity (permittivity) or a material's dielectric constant, or alternatively, electric inductance (permeability). The mass may be any phase or combination of phases. The mass may be stationary or flowing. It may comprise discrete particles such as grain, or manufactured products such as ball bearings or threaded fasteners, etc. The mass may be a flow element in a rotameter or similar flow measurement device. The sensor comprises a volume which may be completely full or only partially full of the material. The material may be discrete components or a continuum. Sensor signals may be received by existing planter monitoring systems. In some embodiments the flow sensors are positioned external to the application port. In some embodiments sensors may be utilized which are responsive to the refractive index variation of specific chemicals.

50 Claims, 20 Drawing Sheets

(51) Int. Cl.
*G01F 1/64* (2006.01)
*G01F 1/66* (2006.01)
*G01F 1/684* (2006.01)
*G01F 11/00* (2006.01)
*G01R 27/26* (2006.01)
*G01N 22/04* (2006.01)
*G01N 11/00* (2006.01)

(56) References Cited

U.S. PATENT DOCUMENTS

| | | | | |
|---|---|---|---|---|
| 4,732,543 A | * | 3/1988 | Hrycyshyn | B67D 1/07 324/607 |
| 5,070,702 A | | 12/1991 | Jackson | |
| 5,134,691 A | * | 7/1992 | Elms | G06F 13/4269 709/209 |
| 5,247,837 A | * | 9/1993 | Corpron | G01F 1/584 73/861.11 |
| 5,488,817 A | * | 2/1996 | Paquet | A01D 41/127 56/10.2 R |
| 5,691,484 A | * | 11/1997 | Feller | G01F 1/584 73/861.13 |
| 5,716,272 A | * | 2/1998 | Nelson | G01N 22/04 460/149 |
| 5,871,397 A | * | 2/1999 | Nelson | G01F 1/663 460/7 |
| 5,906,732 A | * | 5/1999 | Kohno | B07C 5/361 137/883 |
| 5,967,066 A | * | 10/1999 | Giles | A01C 23/024 111/119 |
| 6,208,255 B1 | * | 3/2001 | Conrad | A01C 7/105 111/903 |
| 6,354,150 B1 | * | 3/2002 | Rudent | G01F 1/6847 73/202.5 |
| 6,386,127 B1 | * | 5/2002 | Prairie | A01B 71/02 111/167 |
| 7,152,540 B1 | * | 12/2006 | Sauder | A01C 7/206 111/170 |
| 2004/0040385 A1 | * | 3/2004 | Hofmann | G01F 1/584 73/861.08 |
| 2005/0000277 A1 | * | 1/2005 | Giles | A01C 23/047 73/114.48 |
| 2007/0044572 A1 | | 3/2007 | Davis et al. | |
| 2010/0145636 A1 | * | 6/2010 | Nyfors | G01F 1/584 702/49 |
| 2011/0184551 A1 | * | 7/2011 | Kowalchuk | A01C 7/105 700/219 |
| 2012/0036914 A1 | * | 2/2012 | Landphair | A01C 7/081 73/1.16 |
| 2012/0169353 A1 | * | 7/2012 | Sauder | A01C 7/105 324/629 |
| 2013/0269578 A1 | * | 10/2013 | Grimm | A01C 7/06 111/127 |
| 2017/0251656 A1 | | 9/2017 | Kolb et al. | |

* cited by examiner

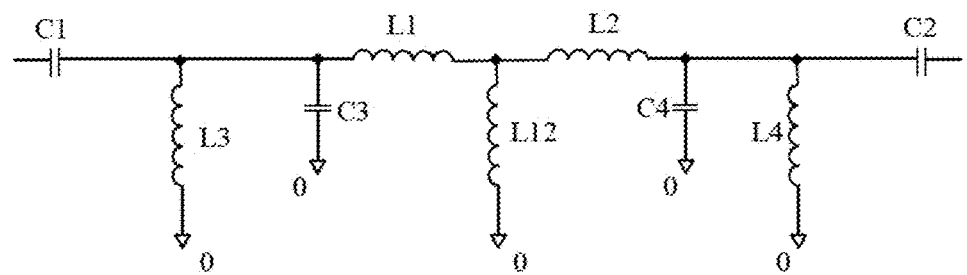
Fig. 33 3300
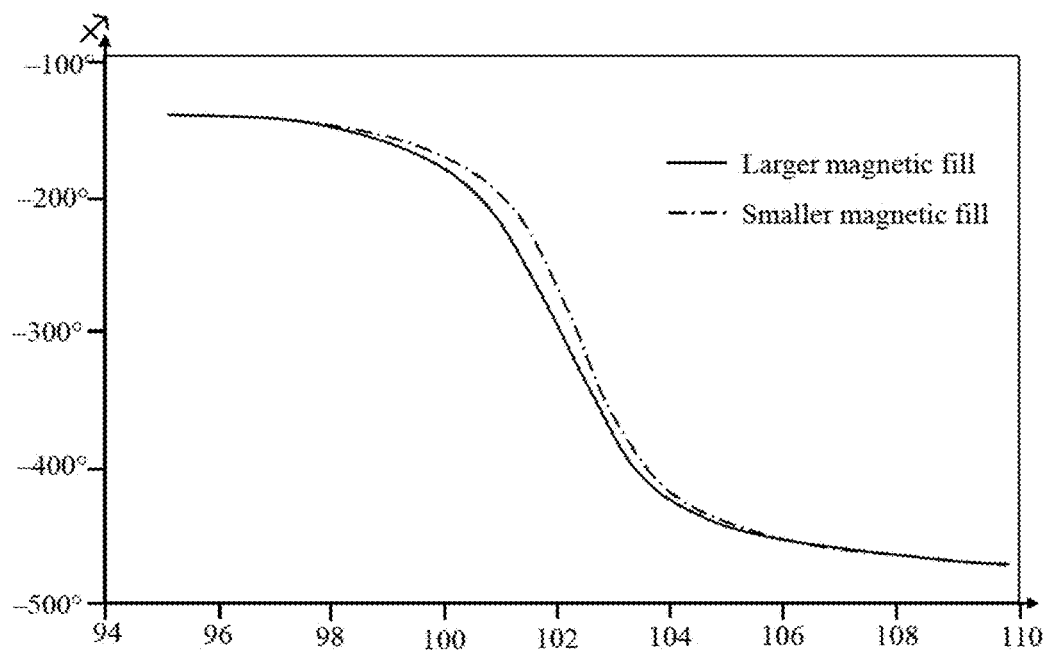
Fig. 34 $f$[MHz]

FLOW SENSOR BASED ON ELECTRICAL CAPACITY

CROSS REFERENCE TO RELATED APPLICATIONS

This application is a continuation-in-part of and claims priority of U.S. Ser. No. 14/037,680, filed Sep. 26, 2013. The entire contents of U.S. Ser. No. 14/037,680 is incorporated herein by reference in its entirety.

BACKGROUND OF THE INVENTION

Field of the Invention

The present invention relates generally to a flow sensor. More particularly the present invention relates to a method and apparatus for sensing the flow rate of fluids, granular solids, and discrete particles by measuring electrical capacity for dielectric materials and magnetic permeability for magnetic materials.

Background Art

The dielectric constant of a first material is usually different than that of a second material. The dielectric constant for a substance may vary depending on the thermodynamic state of that substance, such as its state: solid, liquid, or vapor (gas). Therefore, the presence of a material may be detected by a process by which its effective dielectric constant is determined. The state of that material may also be deduced from the value of the effective dielectric constant. Similarly, for magnetic material, the presence of a material may be detected by a process by which its effective relative permeability is determined. The state of that magnetic material may also be deduced from the value of the effective relative permeability of the material.

Anhydrous ammonia is a popular choice for providing nitrogen to crops—particularly corn—in the Midwest. Other forms of nitrogen are applied in liquid form, both during planting and as a side dressing.

For a state such as Iowa, the average annual export of nitrate from surface water in Iowa was estimated to range from 204,000 to 222,000 Mg, or about 25% of the nitrate the Mississippi river delivers to the Gulf of Mexico, despite Iowa occupying less than 5% of its drainage basin [K. E. Schilling and R. D. Libra. *Increased baseflow in Iowa during the second half of the 20th century*. Journal of American Water Research Association, 39:851860, 2004]. Therefore, controlling the flow rate of anhydrous and other nitrogenous fertilizers is paramount to avoiding nitrification of surface and ground water.

Iowa State University published an article describing the difficulties of anhydrous ammonia application entitled, "Improving the uniformity of anhydrous ammonia application," Publication Number PM 1875, dated June 2001. This publication is hereby incorporated in its entirety by reference.

When insufficient anhydrous ammonia is applied to a crop row, that field strip (area) will not yield as it should and the costs incurred from tillage, planting, and harvesting are an economic disadvantage. Again, controlling the rate of application is crucial for the production of food stuffs on the farm.

Sensing the flow of anhydrous ammonia is one application of the sensor of the present invention. U.S. Pat. Nos. 6,208,255 and 6,346,888, both of which are hereby incorporated by reference, discuss how to use near resonance microwave techniques for flow measurements. Most row-crop agricultural equipment for the application of anhydrous ammonia is not provided with flow sensors for individual rows. Additionally, liquid spray agricultural equipment does not provide for individual row sensing.

Considering anhydrous ammonia application systems, present single-sensor systems measure mass per acre but row to row variations can run as much as 30%. Present day anhydrous ammonia applicators use cooling towers or cooling chambers and pressurized systems or combinations of the two. One common system used has cooling towers or devices that use bleed off of 5 to 10% of the ammonia vapor for liquefying the remaining anhydrous ammonia. The bled vapor is often injected along with the measured ammonia resulting in over-application. Also, after the liquid anhydrous ammonia leaves the cooling chamber and flow sensor, vaporization may again occur. This results in varying rates of application due to many factors such as heating of the applicator hoses. In order to keep the flow rate to each row similar, often identical length hoses are used. Hoses for short distances are coiled while hoses for longer distances are straighter. However, unless the hoses are held parallel to ground, anhydrous ammonia liquid will pool in low regions resulting in differential flow rates. Also there is no easy way to tell if the hose on a particular row is plugged because the rate controller keeps the total rate constant even if an individual hose is plugged.

Totally pressurized systems for anhydrous ammonia are available and provide liquid flow through the flow sensor system. However, these systems are more costly and require more maintenance. They also do not typically have row plugging detection. Augmenting such systems (hybrid systems) with delivery pumps to maintain pressure for higher rates is costly, as well as more complex, resulting in poorer reliability.

Anhydrous ammonia applied by a typical system is nominally 90% vapor and 10% liquid by volume, but nominally 90% of the mass of the applied ammonia is in the liquid form. These properties make flow sensing challenging.

Sensing the flow rate of particulate matter, such as grain has proven a challenge as well. Inaccurate sensing of individual grains in a planter can result in overpopulation or sparse planting—neither of which is advantageous to the farmer.

Poor measurement of other substances may have alternate adverse impacts in other applications. It is therefore very advantageous when a flow monitoring systems can detect non-uniformity of flow and, where applicable, is used to control and/or adjust flow uniformity.

There is, therefore, a need for an improved method and apparatus for sensing fluid flow—liquid, vapor, or solid, or a mixture—to provide for uniform application of the fluid.

BRIEF SUMMARY OF THE INVENTION

An object of the present invention is to provide a method and apparatus for sensing fluid and particulate flows. An additional object of this invention is to measure the mass of a material whether the material is stationary or flowing. An additional object is to provide a flow sensing system that does not require cooling towers or other phase-change apparatuses to effectively sense flow rate. Still another object is to detect a path traveled by a particle such as a single grain or a bubble within a liquid.

A measure of the presence and amount of a substance in a specified volume can be made by measuring the capacity between two electrical conducting plates positioned on the periphery of that volume. It is not necessary that the plates be directly opposed to one another. However, for example, a volume consisting of a rectangular cross section (one long side and one shorter side) could have electrical conducting plates along each long side and electrical non-conducting plates along the shorter sides. The surfaces on the third dimension of the volume are usually such that the substance to be measured could move into and out of the volume.

In one preferred embodiment, these third dimension surfaces consist only of virtual surfaces through which mass is permitted to pass. At least two such sensing volumes may exist in close proximity to one another and disposed in a streamwise direction from one another. In order to measure flow of a substance or material whose density varies with time, the amount of material would be measured in a first sensing volume and then, as the substance flows, that material would be measured subsequently in a second sensing volume. A cross correlation in time between the amounts of material in each of the volumes would indicate the flow velocity and mass divided by the cross-sectional area multiplied by the velocity would be the mass flow rate.

This flow determining technique has been used in U.S. Pat. Nos. 6,208,255 and 6,346,888. The sensors are placed sufficiently near one another that any variation of material density is minimized over the time taken to traverse the distance between the two sensing volumes.

The sensors placed on the sensing volume measure the electrical capacity of the substance within the sensing volume. Knowing the dielectric constant of the material (analyte) within the volume, a determination of the dielectric mass can be made, and thus an inference to the material mass within the volume. Knowing the mass and volume, the density of the material is easily extracted. To calculate a mass flow rate, all that is required is a velocity.

A particular challenge is that of determining the mass flow rate of a saturated liquid-vapor mixture. A saturated liquid-vapor mixture is defined as a mixture in which liquid and vapor are in equilibrium with one another. The cases of pure saturated liquid alone and pure saturated vapor alone are included in this definition.

The subjects of equilibrium and saturated liquid-vapor mixtures are covered in undergraduate thermodynamics courses, and are included in any textbook used for such a course. An example text is "Fundamentals of Engineering Thermodynamics," Moran and Shapiro, Wiley, $7^{th}$ edition, 2011, which is herein incorporated in its entirety by reference.

In particular, the quality of a saturated mixture is defined as:

$$x = \frac{m_g}{m_g + m_f}$$

where $m_f$ is the mass of the liquid in the mixture and $m_g$ is the mass of the vapor in the mixture. Hence, $m_g + m_f$ is the total mass of the mixture. The density, $\rho$, of a saturated mixture is related to the quality as follows:

$$\rho = \frac{\rho_g \rho_f}{(1-x)\rho_g + x\rho_f}$$

where $\rho_f$ is the saturated liquid density and $\rho_g$ is the saturated vapor density. The mass of a substance with a density, $\rho$, within a volume, $V$, is:

$$m = \rho V,$$

irrespective if the substance is solid, liquid, vapor, or any combination of these.

Saturated substances, such as anhydrous ammonia as applied to agricultural fields, may experience a change in quality, and hence, dielectric constant (permittivity) as they flow inside their respective conduits. Using the mass or density results from a single measurement volume, outlined above, and using another technique to measure velocity or a value related to velocity provides mass flow rate.

For materials like anhydrous ammonia (or mixtures of anhydrous ammonia and water or other materials) mass flow rate depends on the temperature or pressure of the fluid such that similar masses would exist in a volume as a saturated liquid-vapor mixture depending on internal temperature or internal pressure. The measurement of mass would then depend on the knowledge of the dielectric constant of each phase and the volume of each phase.

In the art, measurements using techniques other than capacity (permittivity) measurement for materials like anhydrous ammonia, the material is converted to a single phase, for example, by cooling, and then the material flow rate is measured. In applications such as an anhydrous ammonia applicator for crop (field) injection, one concern is uniformity of application between various rows formed by individual injectors. In that application, monitoring and/or controlling parameters such as pressure and/or temperature enhance the uniformity of measurement results.

For example, in one preferred embodiment, a manifold with a single input in which flow rate is measured using a two sensing volume technique or an alternate technique, and a multiplicity of outputs for which the quality of the substance varies and in which similar pressures and temperatures exist allows uniformity of flow between the multiplicity of outputs to be monitored. In an agricultural application, uniformity of anhydrous ammonia is a primary concern. Excess amounts of nitrogen (one source is anhydrous ammonia) do not increase crop production but contribute to run-off.

In the discussions to follow, time-delay is meant to be the time-delay between an input signal to the measurement path and the output signal from the measurement path. Since the system is causal, the time-delay is positive, however, differential time-delay, being the derivative of radian phase shift with respect to radian frequency, might be negative.

$$t_d = -\frac{\theta}{\omega} = -\frac{1}{360}\frac{\phi}{f}$$

$$\tau_d = -\frac{d\theta}{d\omega} = -\frac{1}{360}\frac{d\phi}{df}$$

Here $\theta$ is the radian phase shift of the output signal with respect to the input signal, $\phi$ is the phase shift in degrees, $\omega$ is the measurement radian frequency (in rad/s), f is the frequency (in Hz), $t_d$ is the time-delay, and $\tau_d$ is the differential time-delay. Either of these time-delays may be correlated to a dielectric constant which can be used to infer material density.

In one embodiment of the present invention, electrical capacity measurement is used to infer density and another form of sensor yields velocity or volumetric flow rate. In another embodiment of this invention, two electrical capacity sensor volumes are used, spaced a known distance apart to determine velocity.

The mass flow rate, ṁ, of a substance is related to the density, ρ, and velocity, ∇, or the volumetric flow rate, $\dot{V}$, as follows:

$$\dot{m} = \rho \nabla A = \rho \dot{V};$$

where A is the cross sectional area of the volume perpendicular to the flow direction.

In still another embodiment, discrete particles are sensed as they pass and may be time stamped for, for instance, grain planting equipment.

A further embodiment of the present invention provides for locating a particle's path, said particle being, for instance, a single seed or grain or a bubble within a liquid. In this case, the two electrical conducting plates are tapered. Hence, the distance the particle travels between the plates at one side of the volume is greater than the distance at the other side of the volume. The signature of the particle's passing on one side of the volume is detectibly different than the signature when the particle passes on the other side of the volume.

In a further embodiment a flow sensor apparatus is provided for monitoring a directed stream from an application port, the directed stream having a target directed portion and an off-target portion. The flow sensor apparatus includes: a) a first electrically conductive plate; b) a second electrically conductive plate disposed a distance away from the first electrically conductive plate; c) a first electrically nonconductive surface disposed to connect edges of the first and second electrically conductive plates; d) a second electrically nonconductive surface disposed to form a volume, the volume bounded by surfaces including the first electrically conductive plate, the second electrically conductive plate, the first electrically nonconductive surface, and the second electrically non-conductive surface; e) a signal conditioning circuitry, having an input and an output, with the first and second electrically conductive plates; f) means for measuring the time-delay from the input to the output of the signal conditioning circuit; g) means for correlating the measured circuit time-delay to the electrical capacity between the two electrically conductive plates; h) dielectric constant determining circuitry to determine an effective dielectric constant between the first and second electrically conductive plates; and, i) a computational function to correlate the effective dielectric constant to a presence of material inside the volume. The first electrically conductive plate, the second electrically conductive plate, the first electrically nonconductive surface, and the second electrically nonconductive surface are positioned external to the application port.

In another aspect the present invention is embodied as an agricultural product application system. In such an embodiment movable application equipment is provided including a flow sensor apparatus for monitoring a directed stream from an application port. The directed stream has a target directed portion and an off-target portion. At least one upwind moisture/humidity sensor is positioned upwind of the movable application equipment. At least one downwind moisture/humidity sensor is positioned downwind of the movable application equipment. In another embodiment sensors may be utilized which are responsive to the refractive index variation of specific chemicals.

The novel features which are believed to be characteristic of this invention, both as to its organization and method of operation together with further objectives and advantages thereto, will be better understood from the following description considered in connection with the accompanying drawings in which a presently preferred embodiment of the invention is illustrated by way of example. It is to be expressly understood however, that the drawings are for the purpose of illustration and description only and not intended as a definition of the limits of the invention.

BRIEF DESCRIPTION OF THE SEVERAL VIEWS OF THE DRAWINGS

FIG. 33 is a circuit diagram of a sensor for detecting permeability; and

FIG. 34 is a plot of (φ,f) for two substances having unequal magnetic fill in the sensor volume.

DETAILED DESCRIPTION OF THE INVENTION

Figure 1:
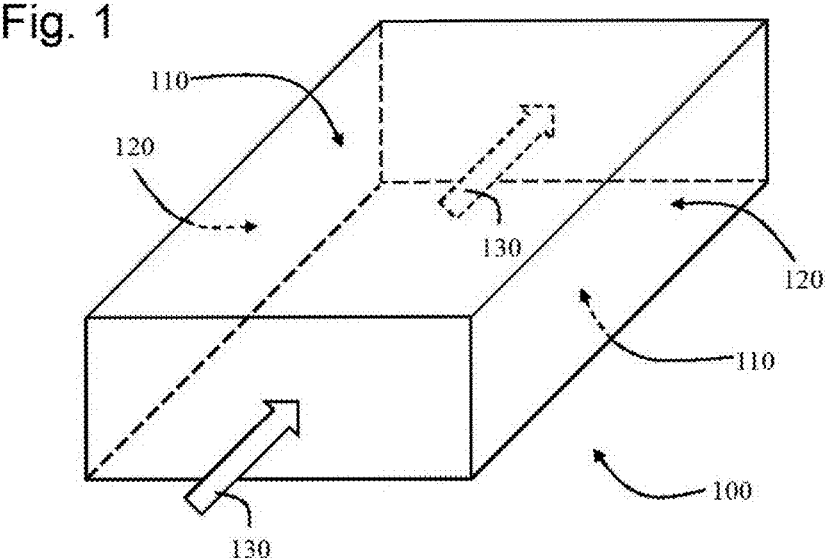
FIG. 1 is a perspective view of a capacity sensing volume of the present invention.
Figure 3:
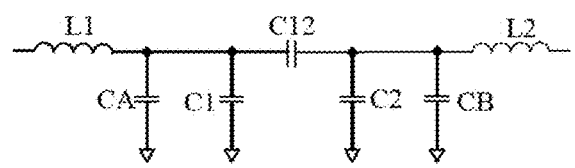
FIG. 3 is a circuit diagram of a first preferred embodiment of the present invention.
Figure 5:
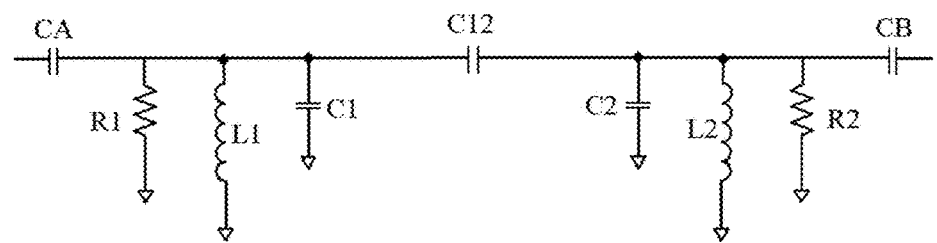
FIG. 5 is a circuit diagram of a second preferred embodiment of the present invention.

A sensor system volume 100 through which material may pass or in which material or matter is contained is shown in FIG. 1. Two sides 110 comprise electrically conducting plates. Two more sides 120 comprise electrical insulators. The capacity between the electrically conducting plates may be measured using methods commonly understood by those of ordinary skill in the art and explained in undergraduate electrical engineering texts. Circuits for this purpose are shown in FIGS. 3 and 5 and their use described below. The arrows 130 indicate a flow direction, but the direction is immaterial. In fact, there may be no flow at all.

Figure 2:
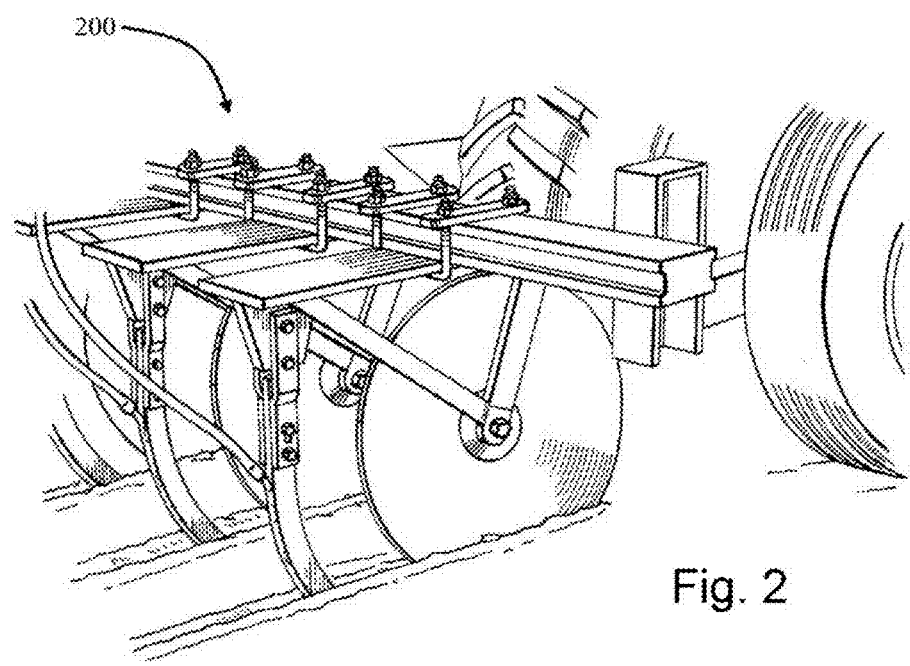
FIG. 2 is a perspective view of an anhydrous ammonia applicator for row crops.

An application of the present invention is the sensing of mass flow rate of anhydrous ammonia using an applicator 200, an example of which is shown in FIG. 2. Such an applicator is made to apply anhydrous ammonia to multiple rows, simultaneously.

An example equivalent circuit of the sensor of the present invention is shown in FIG. 3. An input alternating currents signal or summation of various alternating current signals known as a Fourier series signal is incident on the left side of the circuit and an output signal would flow from the right side of the circuit. The frequency (frequencies) of the alternating current signal(s) may be from just above zero (direct current) to well into the optical region. Not shown is the input source or the terminating load. The input source and terminating load can be a fairly simple source and a terminating resistor. At other times, the source might consist of a power splitter allowing some of the power from a source to enter the circuit and other parts of the power to enter part of an amplitude-phase measuring circuit. The terminating circuit might consist of a transmission line, other components, and a subsequent termination. The subsequent termination might be in the amplitude-phase measuring circuit.

Under the multitude of configurations, one purpose is to sense the two-port amplitude-phase response of the sensor volume. In many applications, the phase shift of the output signal versus the input signal will result in the desired characteristics being determined for the sensor volume. In other situations, the input reflection coefficient (a measure of how much of the input signal is reflected from the input port) can also be used to determine the characteristics of the volume.

The transmission and reflection parameters of the sensor volume might be determined by scattering parameter techniques, immittance matrix techniques, chain matrix techniques, hybrid matrix techniques, etc., known to those skilled in the art of circuit characterization. L1 and L2 are input and output coupling inductors respectively, CA and CB are input and output circuit matching capacitors, and C1, C12, and C2 are capacitances associated with the sensor volume. In one embodiment, C12 would represent the parallel plate capacity between an input electrode and an output electrode, such as the plates 110 of FIG. 1.

The circuit in FIG. 3 can be represented in the art as a two pole filter wherein C12 is the coupling capacitor between two resonators. The phase shift, at a given frequency, response of this circuit depends on the value of C12. The resonant frequency (for instance the passband center frequency) of the circuit depends on the value of C12. Increasing C12 will lower the resonant frequency of the circuit.

Time-delay at a given frequency is related to phase shift through the circuit by:

$$t_d = -\frac{\theta}{\omega} = -\frac{1}{360}\frac{\phi}{f}$$

where $t_d$ is the time-delay through the circuit, θ is the phase shift through the circuit, and ω is the measurement frequency used.

Figure 4:
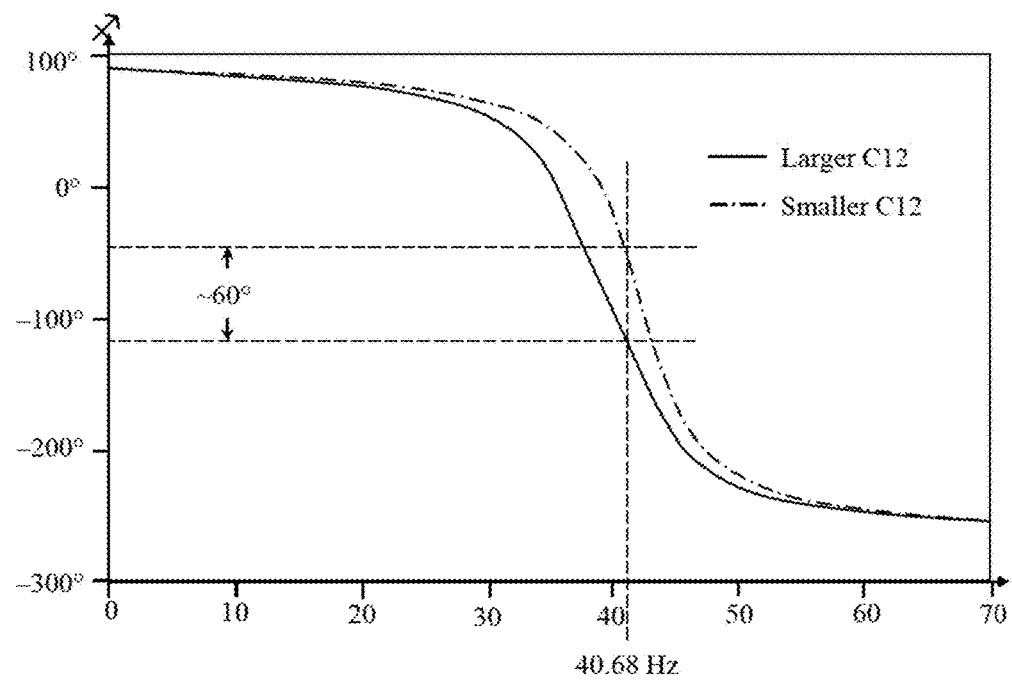
FIG. 4 is a first plot of (ϕ,f) for two substances having unequal dielectric constants.

A typical curve of phase shift versus frequency for the circuit is shown in FIG. 4 where the left most curve results from a C12 larger than that for the right most curve. At 40.68 MHz (an ISM frequency), this sensor shows a variation of, nominally, a negative 60 degree phase shift to negative one-hundred twenty degrees phase shift. This results in a change in time-delay due to a change in phase shift at the same frequency.

In one embodiment of the sensor, the time-delay can be measured with the use of a phase frequency detector using two D flip-flops and one "and" function as is well known to those versed in the art. This time-delay is a function of the dielectric fill in the volume of the sensor 100.

For those applications wherein the analyte is a continuum (solid, liquid, vapor, or gas) the time-delay is a function of the permittivity of the material. For other applications where only the variation between a plurality of sensors is to be indicated or measured, the uniformity of time-delay between various sensors is the desired item.

In a preferred embodiment, the time-delay of the signal is less than the period of one cycle of the signal. As indicated below, in certain embodiments of the sensor, the time-delay might be longer than one period of the signal. Differential time-delay measurements in that case would allow the variation of dielectric fill to be measured.

In those configurations where the time-delay is less than the period of one cycle, and since by causality the time-delay though the second path is positive, a simple "exclusive-or" circuit can be used to measure time-delay of the signal as is well known in the art.

Another embodiment of a sensor volume system would use the equivalent circuit of FIG. 5 with a similar output phase shift versus frequency. The added resistors, R1 and R2 are included to represent loss in the components. Core loss in an inductor manifests itself in an equivalent circuit of an inductor as a resistor in parallel.

Figure 6:
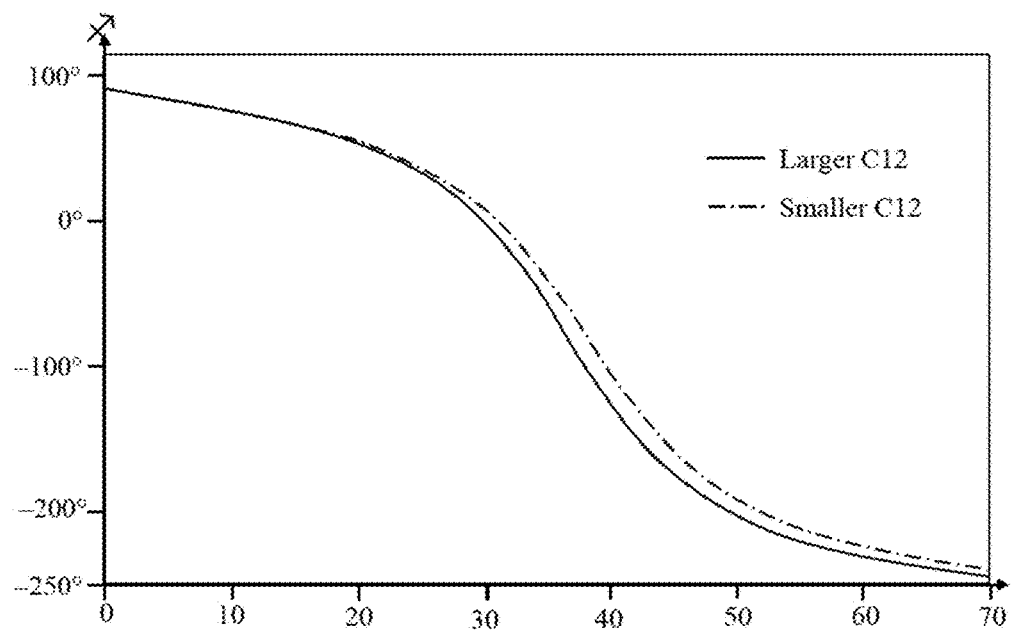
FIG. 6 is a second plot of (ϕ,f) for two substances having unequal dielectric constants.
Figure 7A:
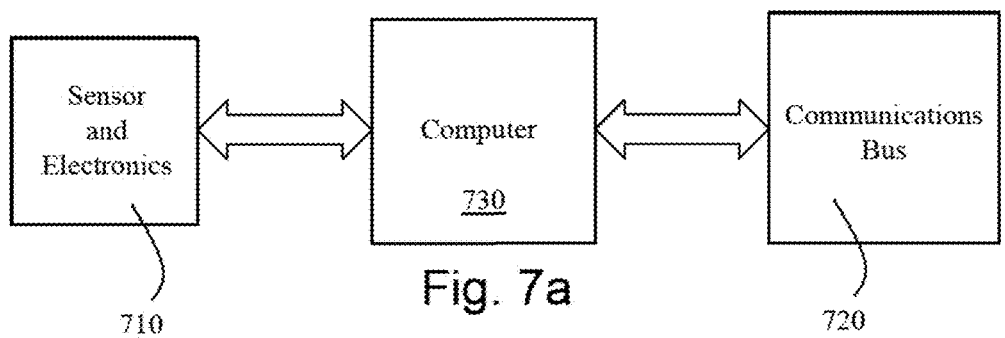
FIG. 7a is a first schematic of a communication and computation flow diagram.
Figure 7B:
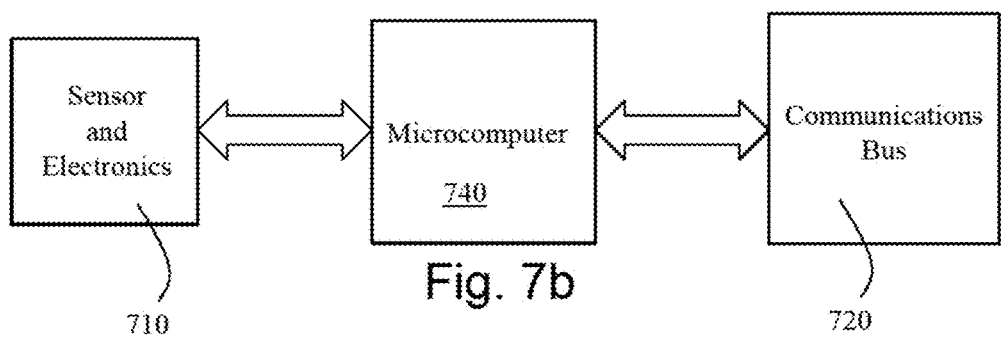
FIG. 7b is a second schematic of a communication and computation flow diagram.
Figure 7C:
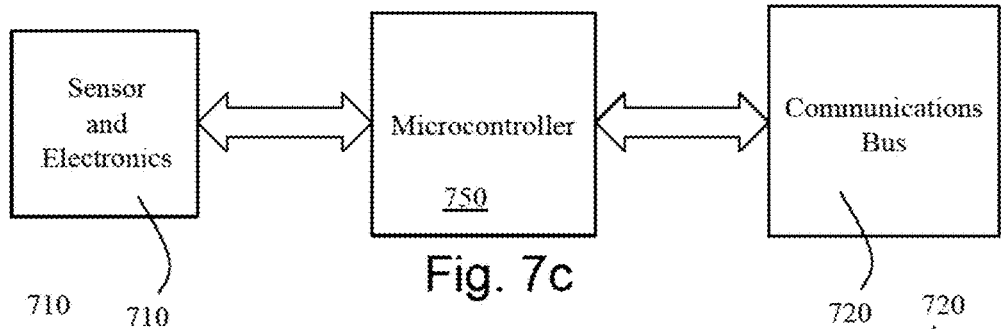
FIG. 7c is a third schematic of a communication and computation flow diagram.
Figure 7D:
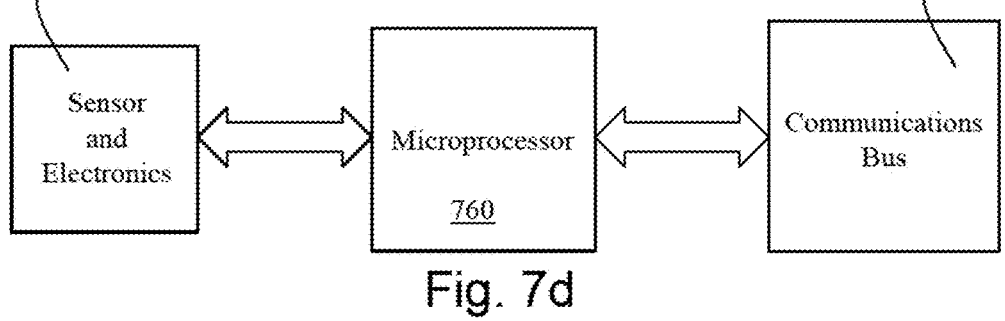
FIG. 7d is a fourth schematic of a communication and computation flow diagram.

The variation in C12 used in the plot of FIG. 6 is different from that used in the first plot shown above. However the phase shift versus C12 can be calibrated to indicate the amount of change in C12 and thus the presence of different dielectric materials in the sensor volume. The value of C12 may be correlated to the nature of the material in the volume.

Various applications may dictate the bandwidth of the sensor, the number of frequency components of the signal of the input source, the sensitivity desired (phase shift versus capacity variation of C12) etc. Various applications might well indicate using alternate frequencies other than 40.68 MHz and still other applications might use more than one measuring frequency, either simultaneously or sequentially.

Other variations are anticipated in application to measuring the permittivity of a volume. In some applications, phase shift might be more easily measurable rather than time-delay. In still other applications, amplitude response of the circuit might be more easily used to indicate volume permittivity. Phase shift and amplitude response are related as well known to those versed in the art. Other sensor circuit configurations could also be used.

As is known in the art, in various applications, the measurement of the impedance (alternately the return loss) at one terminal of the circuit or using only one terminal (rather than two as shown) can often be used to quantify the value of C12 or when the terminal intersection of C2 and C12 is at ground potential, the value of an equivalent C12.

Other embodiments include those for which signal phase can be quantified and measured. Time-delay, by causality, through the circuits would be positive. However, differential time-delay, which can also be measured, might be negative in some regions of the frequency domain. In a preferred embodiment, as shown in the two circuits above, it is time-delay that is measured. The time-delay through the circuit, for instance, using a long transmission line in a return path may make the time-delay longer than one cycle of the signal. The time-delay measured by measuring zero crossings would then be in error by an integer multiple of a period. However, differential time-delay would still give an indication of a change in the time-delay within the measurement cell.

The application of the art discussed here can provide for row to row sensing of anhydrous ammonia or for row to row sensing of other sprayer applications.

Mass flow rate for more complex systems can be determined and is a useful application using the techniques described here. However, in order to simplify and lower the cost of a system for anhydrous ammonia, mass only can be measured for many applications. Ammonia tool bars have a distribution manifold. These manifolds have an input port and several output ports. Mounting a mass flow rate sensor on each output port will monitor the mass flow rate to each row.

Planter monitoring systems are provided land speed information and expect a pulsed signal indicating seed counts from the planter units. The sensor system, in some embodiments of the present invention, when employed to measure mass flow rate, will put out a number or frequency of pulses as a function of the mass flow rate. On the ammonia function the monitor will sense the mass—usually pounds—per acre. When monitoring planting equipment and the flow rate of seeds, the seed monitoring function uses a bar graph function to compare different seed rates for each sensor and sets an alarm if the sensor signals do not conform to the allowable tolerance. Adjusting the flow rate for individual rows can either be done manually by a valve system or electronically with an automatic controller function. Such an automatic control function would employ an automatic control algorithm, such as a Proportional, Integral, Differential (PID) algorithm. The seed function can be reprogrammed to read mass or seed flow rate rather than seeds per acre.

This same function can be used to monitor liquid systems and sprayers except the sensor will be used to determine velocity instead of, or in addition to, mass. In a liquid system the density is substantially constant and the speed of the flow will vary according to the application rate. The sensor will put out a number of pulses according to the flow velocity.

Figure 8A:
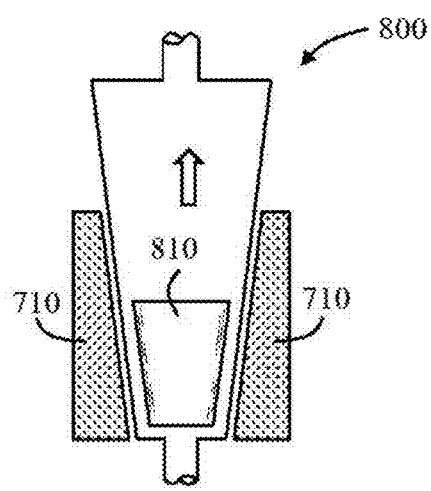
FIG. 8a is a side elevation view of a first rotameter flow measurement device with electrical capacity sensing.
Figure 8B:
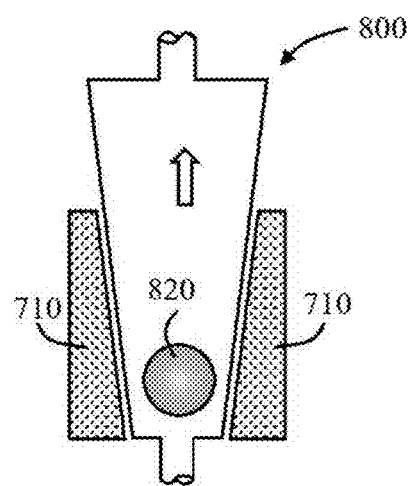
FIG. 8b is a side elevation view of a second rotameter flow measurement device with electrical capacity sensing.
Figure 8C:
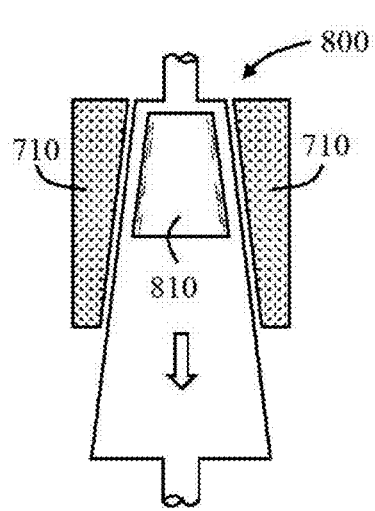
FIG. 8c is a side elevation view of a third rotameter flow measurement device with electrical capacity sensing.

In one embodiment of the present invention the flow sensing system is augmented in various applications with prior art rotameter flow sensors 800 shown in FIGS. 8*a*-8*c* or the like using a truncated cone 810, bead 820, cone, or other shape having a known drag coefficient versus flow rate function. These additional sensors may be mounted vertically to use gravity as the force to position the sensor element, or buoyancy for downward flow, as shown in FIG. 8*c*, or may use spring force to position the sensor element 910 (FIG. 9), 1010 (FIG. 10) for applications where impulse or vibration are non-negligible, or when the installation is necessarily non-vertical.

When microwave frequencies are employed with the present sensor 710 as applied to a rotameter 800 or similar flow meter, when using the proper material, the sensor 710 will respond to the total mass in the sensor volume 100. Since liquids such as ammonia and water have a higher dielectric constant than their respective vapors or air, if vapors are present in the meters 800, the physical movement of the sensor element 810, 820 will correspond to the total volume of the flow. So unlike the standard rotameter 800 false measurement caused by non-liquid flow are eliminated.

Flows of fluids such as ammonia, which can be 90% vapor 1120 and 10% liquid 1110 (see FIG. 11) by volume, a much more accurate flow reading may be obtained without cooling.

Figure 9:
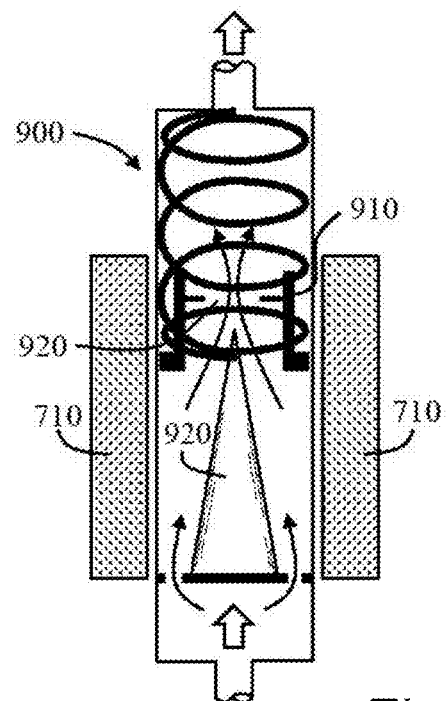
FIG. 9 is a side elevation view of a flow measurement device using a piston-spring assembly and electrical capacity sensing.
Figure 10:
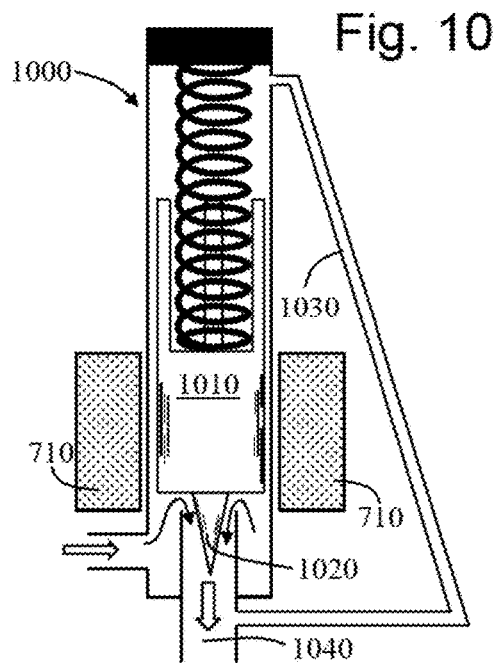
FIG. 10 is a side elevation view of a flow measurement device using a piston-spring assembly that plugs the exit in the absence of adequate pressure and uses electrical capacity sensing.

The flow sensor 900 shown in FIG. 9 makes use of a piston 910 with an orifice 920 providing flow resistance and a consequent streamwise force—against the spring force. The flow sensor 1000 of FIG. 10 makes use of a positive-sealing piston 1010 with a conical plug 1020 and a pressure relief line 1030 to equalize the pressure between the space above the piston 1010 and the flow exit 1040.

The electric capacity sensor 710 of the present invention can be used with these additional sensor elements 800, 900, 1000. The material used in the bead 820, cone 810, piston 910, plug 1010, or other movable component is chosen so the dielectric constant of mass is different from that of the fluid being measured. When the bead 820 or sensing element 810, 910, 1010 is moved by the flow, the resulting position change is detected by the sensor system 710 as described. The location of the sensing element 810, 820, 910, 1010 is a function of the flow rate and is sensed by the increment change in location of the sensing element 810, 820, 910, 1010 material in the measurement volume. The known function of bead or cone location to flow rate is used to calculate the flow rate. This known function is determined by the manufacturer or from empirical data.

Figure 14:
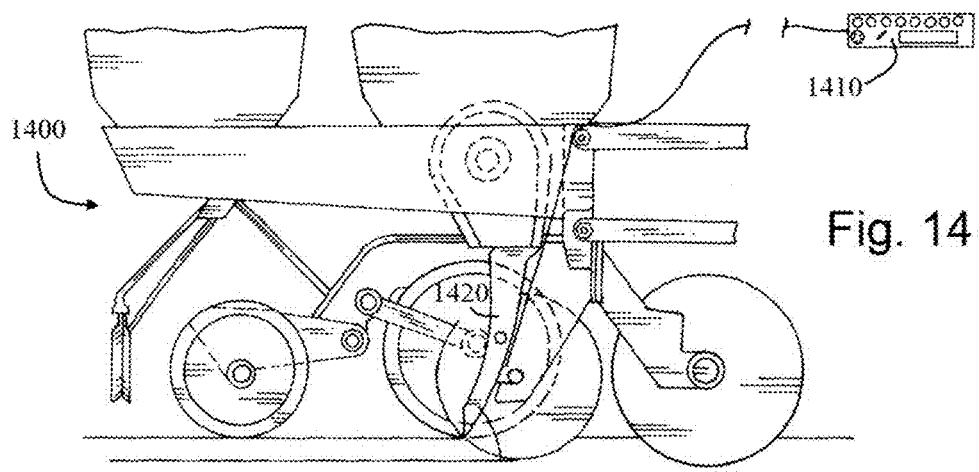
FIG. 14 is a side elevation view of a grain planter.

In addition to the system augmentation in the sensor area, the system interface to other systems and/or vehicles is augmentable with the use of computational machinery as depicted in FIG. 7a-7d. A monitor and operator interface, such as a seed monitor 1410 (FIG. 14) is likely mounted in the space occupied by the operator, such as an agricultural tractor.

Figure 11:
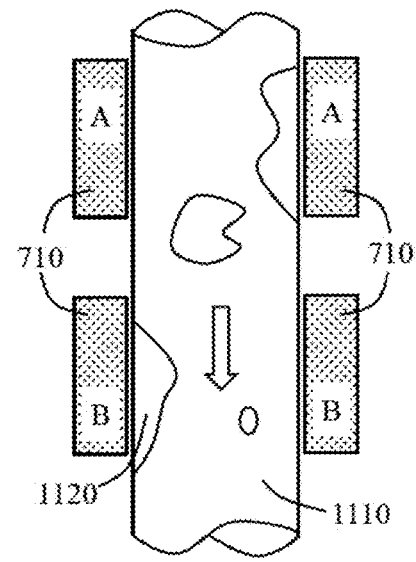
FIG. 11 is a depiction of two-phase flow.
Figure 15:
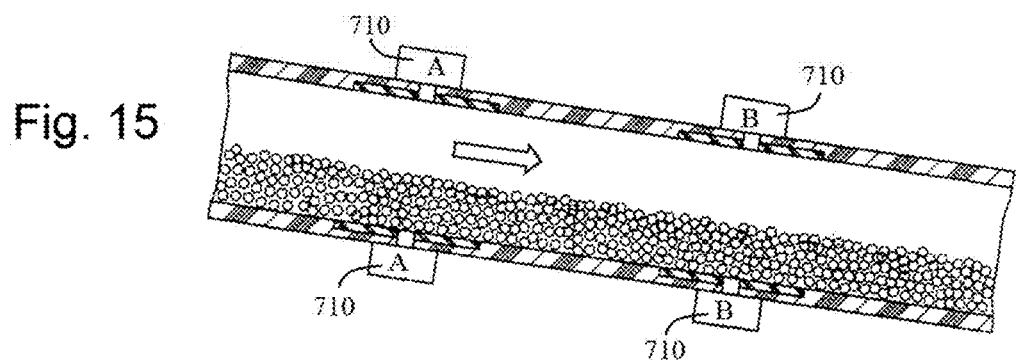
FIG. 15 is a partially filled conduit containing flowing solid particles.
Figure 16:
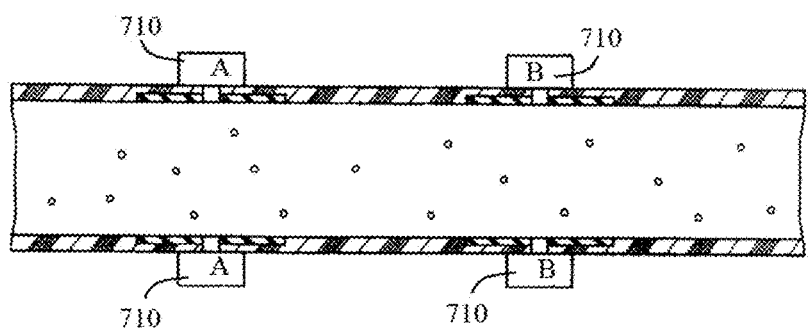
FIG. 16 is a conduit carrying widely dispersed solid particles in a fluid.

The sensor 710 is responsive to various analytes—liquid, solid, particulate FIGS. 12, 13, 15, and 16, liquid/vapor mixtures FIG. 11, etc. The computational machinery of FIGS. 7a-7d can process the various signals from different analytes to give a signal indicative of the thermodynamic properties of the material. The computational functions may be performed by one or more of a computer 730, a microcomputer 740, a microcontroller 750, or a microprocessor 760. For example, the signal from a mixture of liquid 1110 and vapor 1120—see FIG. 11—might be augmented by an input from another sensor, tractor, or implement to account for the characteristics of a particular environment or measurement condition. The signal can be processed to conform to various communication bus 720 architectures for transmission of information. The information may be unilateral or bilateral and might contain control information or commands in addition to signaling information. Referring now to FIGS. 11, 15, and 16, for flow rate determinations of a material or substance flowing as a continuum, the response from Sensor A may look like the noisy signal shown in FIG. 18a, whereas the response from Sensor B may look like the noisy signal shown in FIG. 18b. Using a sampling technique and a correlation technique, a signal similar to that indicated FIG. 18c results. The value of Δt at the peak "G" of this signal is the time required for the material to travel between the two measuring volumes. For high flow rates in which a greater volume of material passes per unit of time, the time difference is less, whereas for lower flow rates, in which a lesser volume of material passes per unit of time, the time difference is greater. In very low flow rates or no flow rate, there would be no discernible signal peak.

Figure 18A:
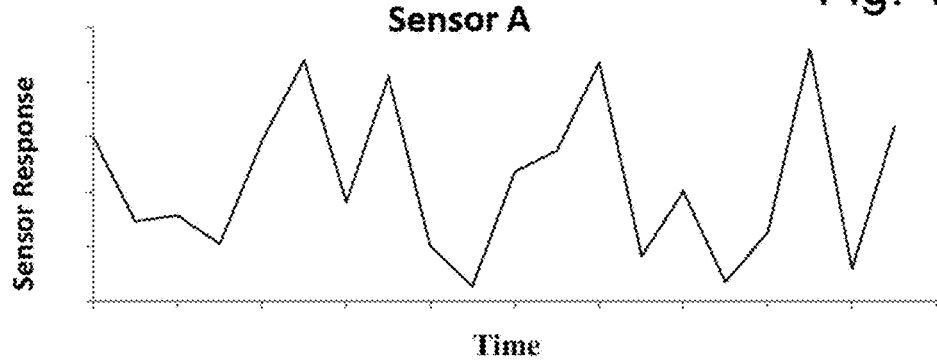
FIG. 18a is a plot of a first sensor response versus time.
Figure 18B:
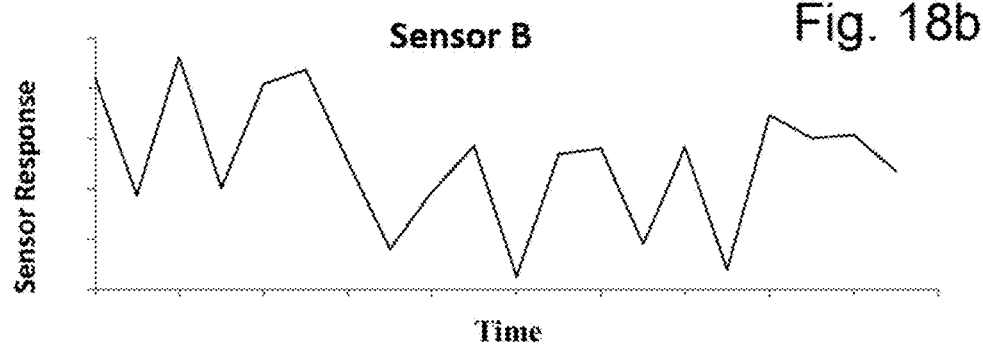
FIG. 18b is a plot of a second sensor response versus time.
Figure 18C:
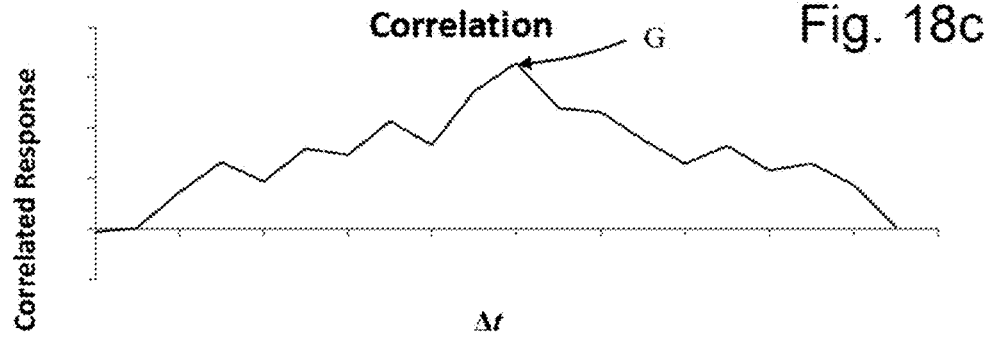
FIG. 18c is a plot of a cross-correlation of the first and second sensor responses versus time increment.

The signals shown in FIGS. 18a and 18b may be received by an operator interface, such as a seed sensor unit 1410. The sampling and correlation may also be carried out in the seed sensor unit 1410, and the pertinent information displayed thereon for the operator. However, the signals of FIGS. 18a and 18b may also be received by any of the computer 730, microcomputer 740, microcontroller 750, or microprocessor 760, and the calculations carried out therein. The results of these calculations may then be sent, via the communication bus 720 to the operator interface unit 1410 for display, alarms, etc. In the latter case, the results of the signal processing must be provided to the operator interface unit 1410 in a form compatible therewith. As those of ordinary skill understand, a seed monitor 1410 provides the operator with information about the performance of the planter and planting operation, such as whether the operation is within tolerance. The same kind of information and alarming would be provided by the operator interface unit 1410 when devoted to anhydrous ammonia application.

Additionally, the sensor system 710 of the present invention may be used in the flow conditions of FIGS. 11, 15, and 16 to sense material density. Given the density, time-delay, and the volume of the measurement volume 100, a mass flow rate may be calculated.

Figure 12:
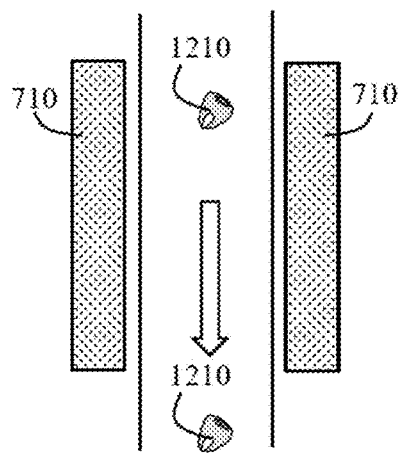
FIG. 12 is a side elevation view of a single-volume detection system for discrete particles.
Figure 13:
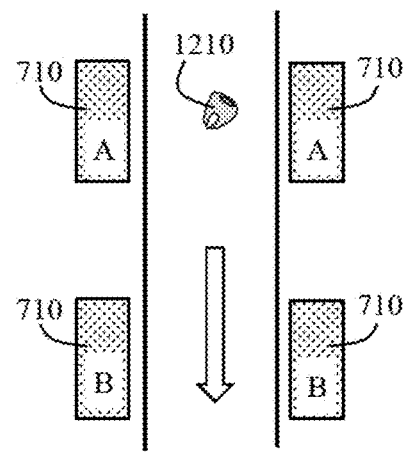
FIG. 13 is a side elevation view of a double-volume detection system for discrete particles.
Figure 17A:
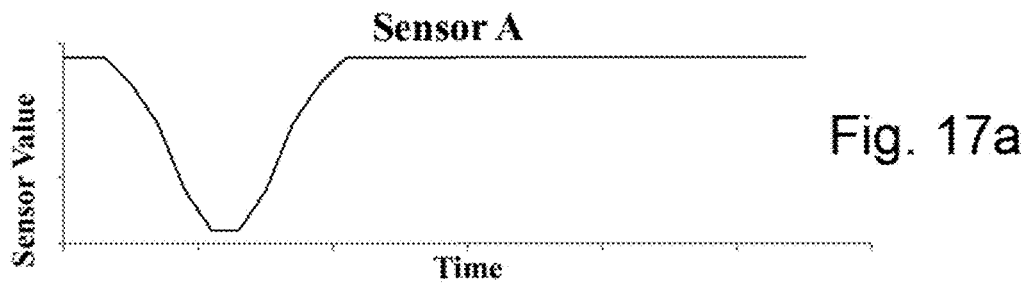
FIG. 17a is a trend line plot showing a first sensor response to a discrete particle.

In FIGS. 12 and 13, an instance of a discrete particle 1210 is shown. An example of this is the planter 1400 of FIG. 14, where grain, such as corn 1210 drops through a conduit 1420. In the embodiment illustrated in FIG. 12, the passage of a particle 1210 is sensed by the sensing system 710 as a change in capacity as shown in FIG. 17a. The signal may be differentiated with respect to time—the first temporal derivative—to obtain a signal such as that shown in FIG. 17c, and the zero-crossing "C" detected to pinpoint the time at which the particle 1210 passed. This time may be compared to the time at which the next (or previous) particle passed to gage the operation of the planter 1400.

Figure 17B:
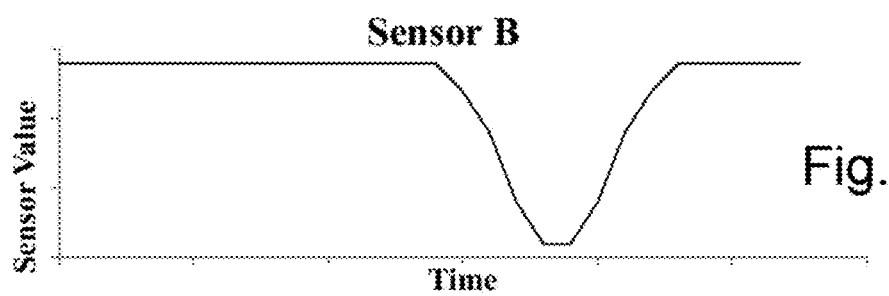
FIG. 17b is a trend line plot showing a second sensor response to a discrete particle.
Figure 17C:
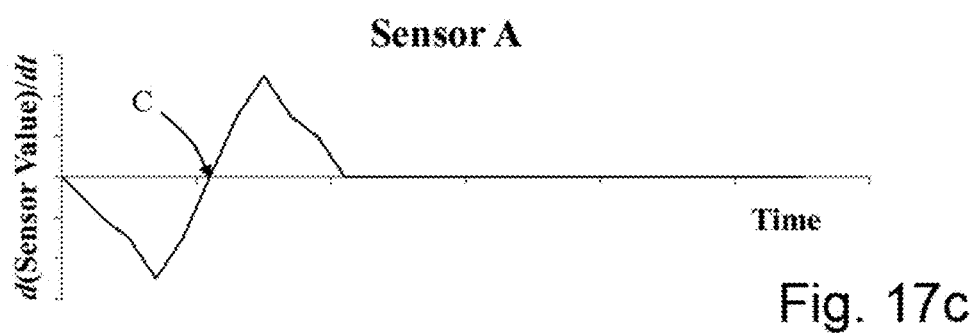
FIG. 17c is a trend line plot showing a first temporal derivative of the first sensor response to a discrete particle.

The signals shown in FIGS. 17a and 17b may be received by a seed sensor unit 1410, as are commonly used to monitor planter performance. The temporal derivatives may also be calculated in the seed sensor unit 1410, and the pertinent information displayed thereon. However, the signals of FIGS. 17a and 17b may also be received by any of the computer 730, microcomputer 740, microcontroller 750, or microprocessor 760, and the calculations carried out therein. The results of these calculations may then be sent to the seed sensor unit 1410 for display, alarms, etc.

Figure 17D:
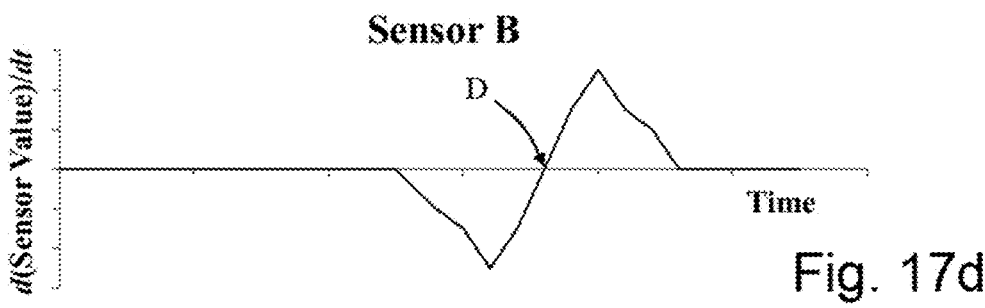
FIG. 17d is a trend line plot showing a first temporal derivative of the second sensor response to a discrete particle.

The embodiment illustrated in FIG. 13, two sensor systems, A and B, 710 are disposed in the flow direction from one another, with sensor system A being upstream of sensor system B. In this case, the signals shown in FIGS. 17a and 17b for sensor system A and B, respectively are sensed. In this embodiment, the signals from both sensors may be differentiated with respect to time to produce the signals in FIGS. 17c and 17d. Again, the time of the zero crossing "C" and "D" for each signal is detected. In this case, the two times of zero crossing are subtracted, indicating the time taken to traverse the distance between the two sensor systems, A and B, 710, thus providing a velocity value.

Figure 19:
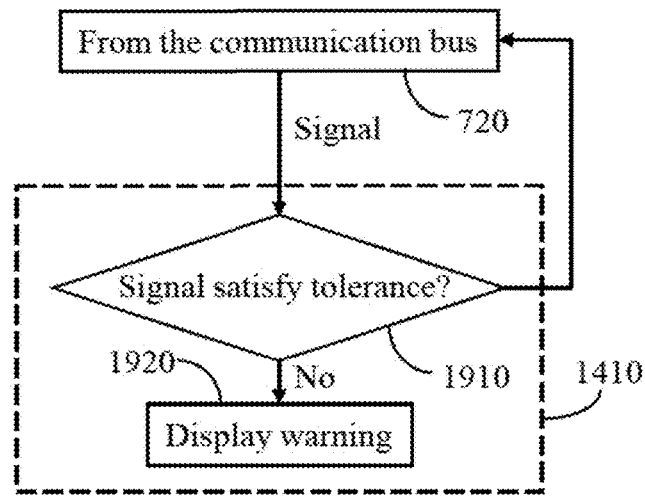
FIG. 19 is a flow diagram illustrating comparing and warning functions.

FIG. 19 illustrates the communication bus 720 communicating with the operator interface 1410. Within the operator interface, the signal is compared to at least one tolerance value in a comparator function 1910. The tolerance value may be a low or high threshold, or both. If the signal does not satisfy the tolerance or tolerances, a warning signal is provided to the operator in a warning function 1920.

Figure 20:
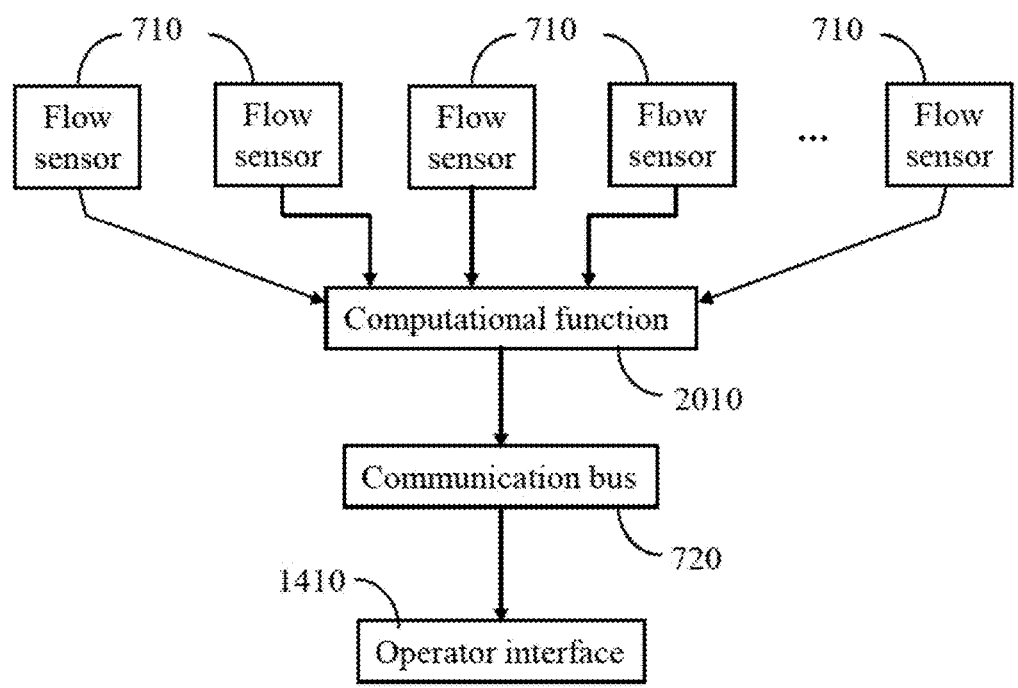
FIG. 20 is a flow diagram illustrating a communication of a plurality of signals from a plurality of sensors.

In FIG. 20, a plurality of sensors 710, are in communication with a computation function 2010 where the signals are processed in an appropriate manner, such as shown in FIGS. 17a-17d or FIGS. 18a-18c. The result is sent, via the communication bus 720 to the operator interface 1410, where the results are displayed, compared, and otherwise made available to the operator in a fashion easily understood. The plurality of signals received from the plurality of sensors 710 may be compared with one another in the comparator function 1910 to determine if the application is substantially even across rows.

The computation function 2010 may, for instance, provide a signal entirely compatible with a seed monitoring system 1410, as used during planting. The seed monitor 1410 may then make comparisons as shown in FIG. 19 exactly the way it carries this function out for the planting operation. Further, the tolerance may be adjusted to satisfy the operator and the needs of the operation.

In many instances, it is important to know not only the presence and size of a particle 1210 being sensed but the path that particle 1210 follows in a tube. For the purposes of this document, including the claims, a particle 1210 is defined as a single solid particle 1210, such as a seed, or a bubble within a liquid. For instance, in a seed planting operation, it is desirable to know that the seed 1210 does not deflect from the tube sides and that its position on exiting the tube can be monitored so its position on planting can be controlled—especially for high planter velocities.

The signal derived from sensing the particle's 1210 position can be used in a feedback control system to control a particle 1210 release mechanism designed to control the particle's path within the volume 100.

Figure 21:
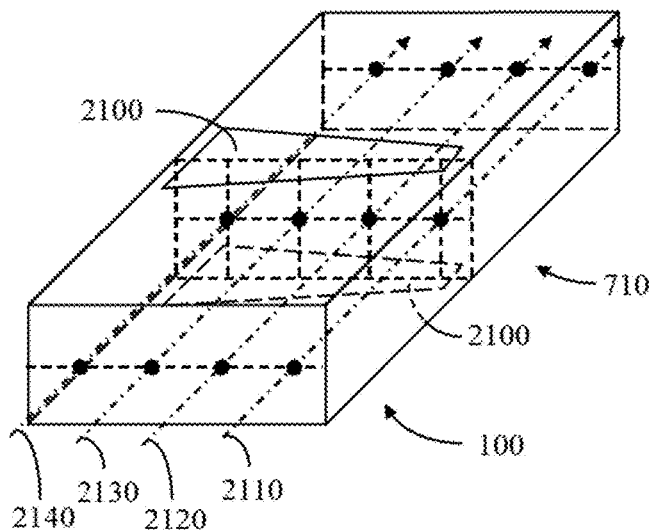
FIG. 21 is a perspective and phantom view of a single-sensor volume using tapered electrodes.

Particulate position may be monitored using the electrical capacity between two tapered plates 2100 such as shown in FIG. 21. It should be noted that the electrical capacity may not be directly measured, but the permittivity of the material filling the sensing volume will change the electrical capacity between the electrodes. This capacity change will change the sensing circuit's response and indirectly the inferred capacity—and thus permittivity—is measured. In a similar manner, if the electrodes were changed to a current loop, magnetic properties in the sensing volume can be measured in a similar manner. Thus, this embodiment involves tapering the two electrically conductive plates in a transverse direction to matter flow; and sensing a transverse location of the matter between the two tapered electrically conductive plates.

Figure 23:
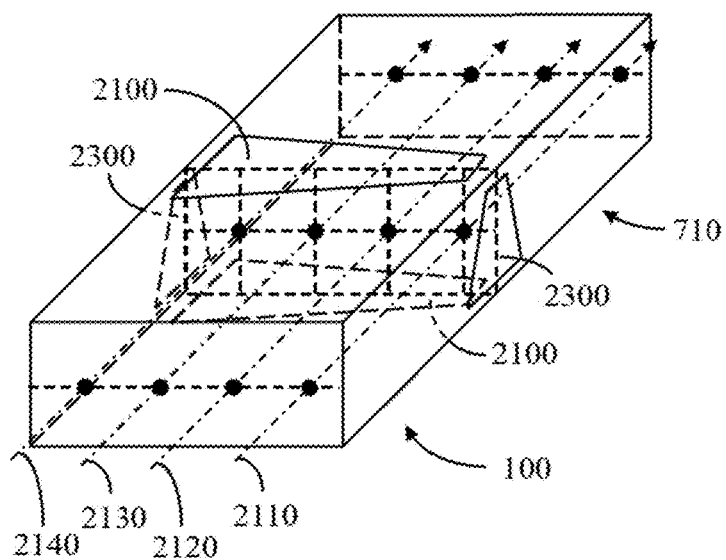
FIG. 23 is a perspective and phantom view of a double-sensor system using tapered electrodes, all at substantially the same longitudinal location, for three dimensional location sensing.
Figure 24:
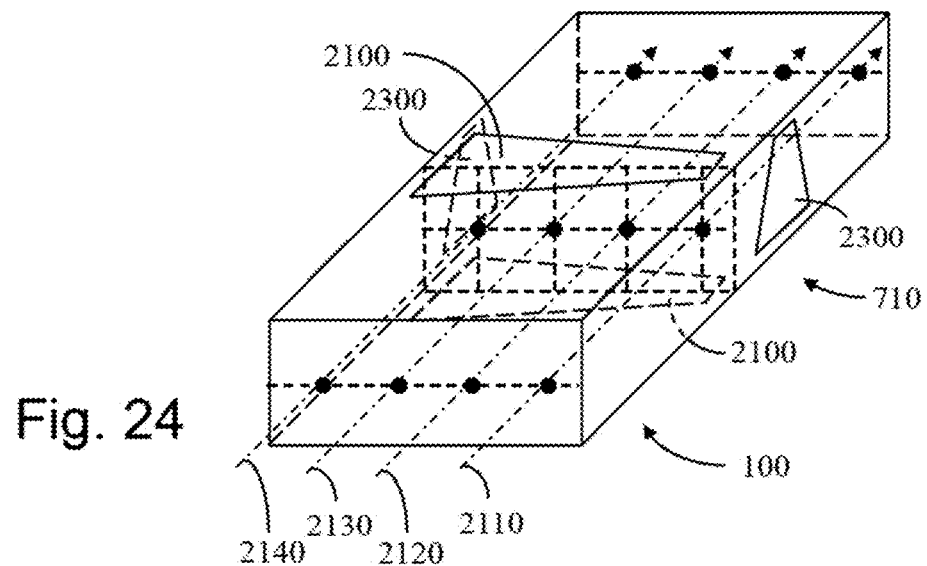
FIG. 24 is a perspective and phantom view of a double-sensor system using tapered electrodes, electrodes for one sensor being upstream of the electrodes for the other sensor, for three dimensional location sensing.

The position sensing system of FIG. 21 may be expanded upon to locate particles in all three dimensions by adding a second sensor on adjacent walls of the volume as shown in FIGS. 23 and 24. Considering the orientation of the volumes of FIGS. 23 and 24, the two tapered plates 2100 indicate location in a horizontal plane while the two tapered plates 2300 indicate location in a vertical plane. It is well understood by those of ordinary skill in this art that the embodiments illustrated in FIGS. 23 and 24 may be disposed in any orientation desired, and are not limited to determining horizontal and vertical positions.

In FIG. 24, the two tapered plates 2100 are shown upstream of the two tapered plates 2300. This arrangement helps avoid electric field interference from the two sensors and may be advantageous in determining particle speed.

Figure 22:
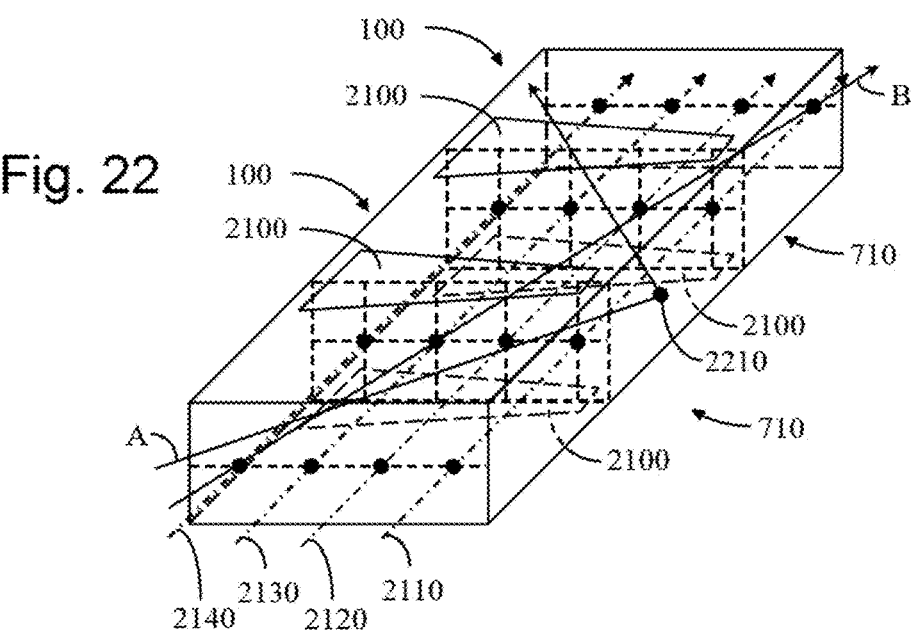
FIG. 22 is a perspective and phantom view of a double-sensor system using tapered electrodes for two dimensional location sensing.

The responses from two such sensors 710, as shown in FIG. 22, in the flow path further help to ensure the particles 1210 follow a path without deflecting from the volume's 100 walls. There are paths particles 1210 may follow having deflections—path A—that provide the same position response signal as a particle flowing without deflections 2110, 2120, 2130, 2140. However, the time between sensor responses differs between that for a direct path 2110, 2120, 2130, 2140 and a path with deflections—path A. A diagonal path A, resulting from a deflection, exhibits a longer path than a direct path 2110, 2120, 2130, 2140 or a diagonal path without deflections—path B—between two sensor volumes 100 and thus a difference in sensed time of travel.

Figure 25:
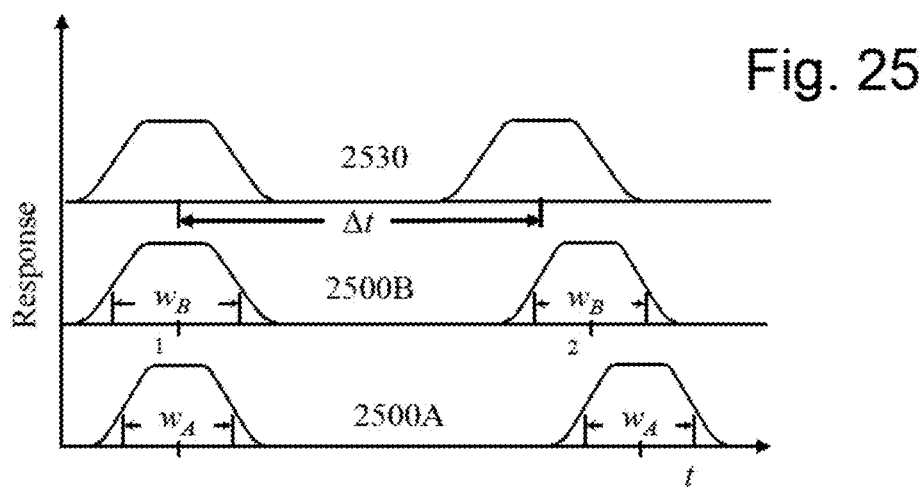
FIG. 25 is a first plot of sensor response versus time for a particle passing through the double-sensor system of FIG. 22 or FIG. 24.

Path B, FIG. 22, shows a path through two sensor electrode volumes 100 that passes at different lateral positions of the two volumes 100 and would be detected as different. FIG. 25 shows three different possible example responses. Note that the top trend 2530, representing a response for path 2130 has two equal amplitude and equal pulse-width responses spaced a time, $\Delta t$, apart. Path 2130 goes directly through the tube, parallel to the longitudinal direction.

Compare the response 2530 to the response for path A, shown as the bottom response 2500A in FIG. 25. Path A includes a deflection 2210 in the path of the particle 1210. There are also two equal amplitude and pulse width, WA, responses shown in trend 2500A except that these pulse responses are farther apart in time than those in response 2530. Predetermined time-delay data stored in the computational function 730, 740, 750, 760, entered manually or computationally determined, permits the system to identify this path as a path with a deflection.

The response for path B, shown as the middle trend 2500B in FIG. 25, has two different width responses, $w_{B1}$, $w_{B2}$, because the particle 1210 passes between the sensing electrodes 2100 of the respective sensors 710 at positions where the sensing electrodes 2100 are of a different width. Also note that the time-delay between the pulses is somewhat longer than the direct path time-delay of response 2530.

Figure 26:
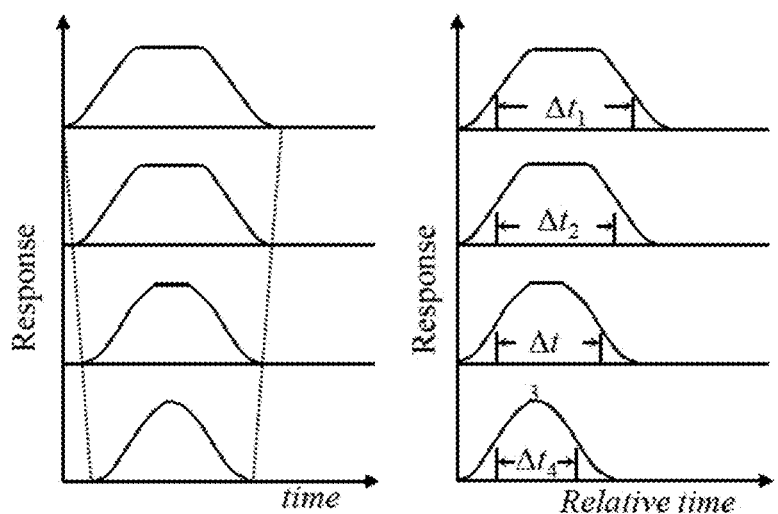
FIG. 26 is a second plot of sensor response versus time for a particle passing through the double-sensor system of the present invention.

Referring now to FIG. 26, the time a particle 1210 takes to pass a virtual plane placed across its path until it approaches the edge of the tapered sensor varies depending on which path within the tube it takes.

The time relationship for the different normalized responses of a single electrode volume 100 shown in the left side of FIG. 26 would result if one plotted the signal response starting at time equals zero when a particle 1210 passes a virtual plane within the tube. The signal then begins to rise as the particle 1210 approaches the edge of the tapered electrode volume 100 and, for different paths, the rise time varies since the distance from the virtual plane to the tapered edge of the electrode varies depending on the particle's 1210 path, i.e., what lateral position the particle 1210 passes between the electrode pair.

However, it is not known a priori when the particle 1210 is approaching the sensor 710. The important parameter of the response is the time difference, $\Delta t_1$, $\Delta t_2$, $\Delta t_3$, $\Delta t_4$, between the time when a particle 1210 approaches the sensor electrode 2100 volume 100 and the time when the particle 1210 leaves the sensor electrode 2100 volume 100 as shown by plotting the responses as seen on the right side of FIG. 26.

Some acceleration of the particle 1210 over the distance traveled within the sensor 710 electrode volume 100 is possible, but with sensor dimensions adequately small with respect to velocity multiplied by time in the sensor volume 100, the differences in velocity may be neglected. In addition, with historical data determined computationally by a system or having been manually inputted, the expected time-delays versus path would be nominally known. For instance, when a particle 1210 undergoes gravitational acceleration, the expected velocity (and thus time knowing the distances) would be nominally known. However, the nominal velocity can also be quantified by knowing the time response between two different sensor 2100 volumes 100 within the flow path.

In applications in which the mechanical design is such that the likelihood of particle 1210 deflection—from conduit walls, for example—is small, it is possible a single tapered electrode 2100 sensor 710 may be adequate to indicate the lateral position of the particle 1210.

By way of explanation, in FIGS. 21 and 22, dashed lines are shown between the sensor electrodes to visually clarify where the flow paths are for the responses shown in FIG. 26 as well as where a particle 1210 is disposed, vertically, in the tube. The paths 2110, 2120, 2130, 2140 shown in FIG. 21 are shown entering a virtual cross-section of the flow tube, progressing through a virtual cross-section between the sensor electrodes 2100 and then exiting the volume 100 via an exit virtual cross-section. Four different flow paths 2110, 2120, 2130, 2140 are shown but there is a multitude of flow paths for a particle 1210 to follow anywhere across the virtual cross-sections, including paths that are at an angle, i.e. not parallel to the longitudinal direction. Sensor 710 responses for particles 1210 will nominally have the same amplitude irrespective on their vertical—as shown in the figures—position at the time of passage.

Figure 27:
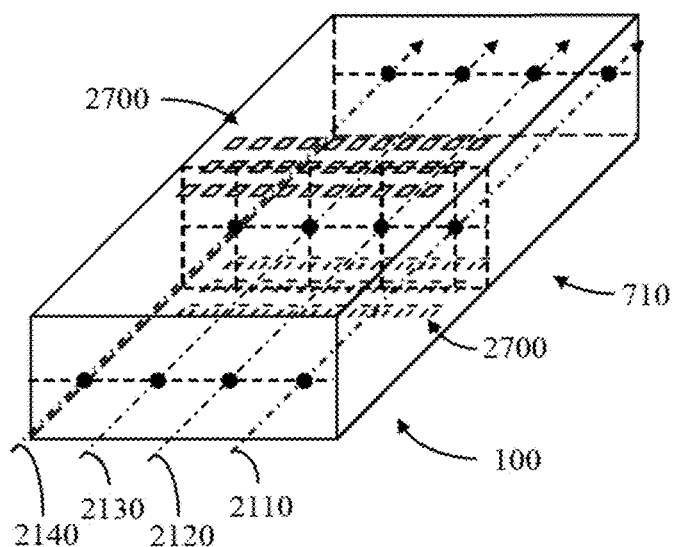
FIG. 27 is a perspective and phantom view of a single-sensor volume using arrays of electrodes.
Figure 28:
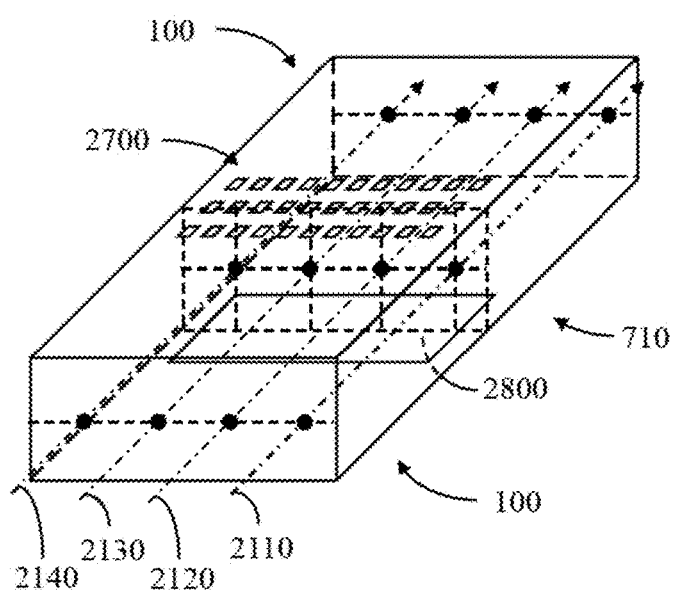
FIG. 28 is a perspective and phantom view of a double-sensor system using one array of electrodes and one single electrode.

FIG. 27 shows a representation of the sensor electrode volume 100 including of two arrays of electrodes 2700. In a similar embodiment, shown in FIG. 28, one of the arrays of electrodes 2700 is replaced by a single electrode 2800 encompassing one of the surfaces. The distance between the individual components of the electrode array 2700 are necessarily small with respect to the array dimensions. If all of the electrodes within an array 2700 on a single side communicate electrically with one another, electrically their summed responses are substantially the same as the response from a single electrode 2800 covering the same area. This is a result of the fringing electrical field existing on the edges of individual electrodes composing an electrode array, or part of an electrode array. Hence, the individual electrodes appear larger than their physical dimensions.

Summing responses from different groups of the arrayed electrodes can make the summed responses appear to simulate a tapered or stepped sensor electrode volume. Summing the responses from a group of electrodes or sensing responses from individual electrodes will thus indicate where, in the volume, a particle 1210 passes.

The time-delay of the responses from electrodes on the entering side and the exiting side indicates average velocity as well. With the computational power available from current computer processors of various forms 730, 740, 750, 760, these measurements and computations can be accomplished with relative ease. The arrayed electrode arrangement is slightly more complex and costly than that of a non-arrayed electrode.

The frequency or frequencies of an alternating current source chosen for the measurement—and thus the signal generator frequency or frequencies—depend on several factors. In order to get a reasonable value of transfer admittance across the measurement volume, the frequency should be sufficiently high that the impedance of the capacity between a set of input and output electrodes 2100 is close to the same order of magnitude as the impedance level chosen for the sensor's 710 circuitry. In many cases, the sensor's 710 detection circuit works at nominally 50 ohms but can be some other value of impedance as well.

Further, the frequency is chosen sufficiently low that the cross sectional areas of the input and output for particle 1210 or fluid flow is small enough that the waveguide formed by the housing (forming an electromagnetic waveguide) does not permit the electromagnetic energy to escape over the input and output areas.

These and other microwave circuit design considerations will often be involved in the choices of frequency and dimensions of the circuit and described in the book, Introduction to Microwave Circuits, Radio Frequency and Design Applications, by Robert J. Weber, IEEE Press, ISBN 0-7803-4704-8, 2001, which is hereby incorporated in its entirety by reference.

Microwave effects might be determined by parasitics or distributed effects associated with the sensor 710 circuit and its components or the choice of measurement frequencies versus sensor 710 size.

The present invention is not limited to any range of frequencies. However, frequencies in the ranges of Radio Frequency (RF) and microwaves may be chosen and, indeed, advantageous. In other applications, optical frequencies may be advantageous.

As indicated above, the sensing electrodes can be changed to loops to directly measure magnetic properties of materials such as magnetic permeability, effective magnetic permeability, etc., by measuring transfer inductance values. In a sensor with two volumes, one volume could measure permittivity values and another volume could measure permeability values of the flow with one volume using capacitance plates and another volume using inductive loops.

When monitoring the transport of magnetic particles or magnetic fluids, e.g. ferrofluids or magnetorheological fluids, it is advantageous to use sensor volumes 100 comprising an inductive loop to sense the amount and/or presence of the material.

For instance, in mangetorheological fluids the ferroparticles may settle under gravity or in a magnetic field. It is desirable to know whether this has transpired and/or the quantity of particles in the fluid. The counting of magnetic particles such as steel screws dropping or flowing into queuing or shipping containers etc. could be accomplished with a magnetic sensor volume.

Figure 29:
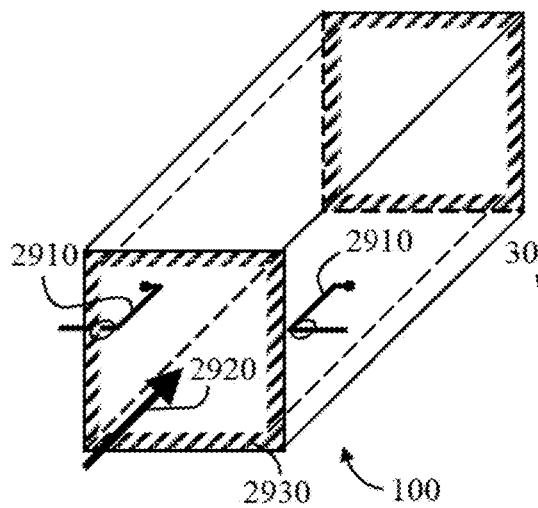
FIG. 29 is a perspective view of a first sensor system for detecting permeability.

FIG. 29 shows a perspective view of a sensor volume 100 with sensing loops 2910 instead of sensing plates 2100, 2700. The sensing loops 2910 may be multi-turn or a simple loop as shown. The sensing loops 2910 generate magnetic fields in the sensor volume 100. Magnetic material passing through the volume will change the mutual impedance of the sensor volume 100 and thus the transmission of electromagnetic energy through the sensor volume 100.

Figure 30:
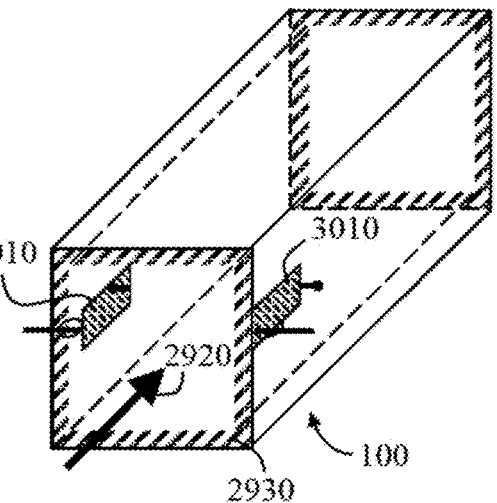
FIG. 30 is a perspective view of a second sensor system for detecting permeability.

In FIG. 30, the sensor loops are shown as small plates 3010 instead of loops. However these plates 3010 are electrically grounded on one end instead of being free floating as in a capacitance measurement. The ball on the end of the loop 3010 is to indicate that the loop 3010 is grounded to the surrounding conducting boundary.

The cross-hatched 2930 area indicates the conducting boundary surrounds a dielectric material that guides the magnetic particles or fluids through the sensor volume 100. The surrounding conducting boundary and the dielectric material that guides the particles or fluid may be rectangular or circular in cross section, as well as having other cross sectional geometries. The present invention is not limited to a particular shape cross section.

Figure 31:
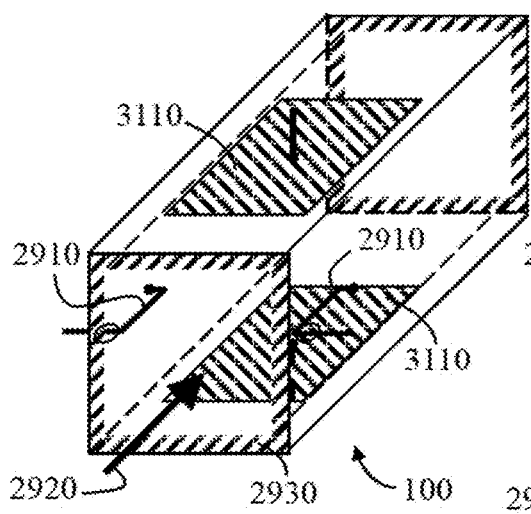
FIG. 31 is a perspective view of a first sensor system for detecting permittivity and permeability.
Figure 32:
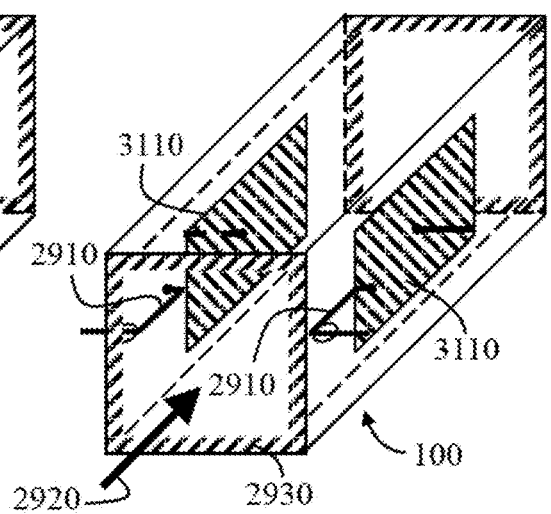
FIG. 32 is a perspective view of a second sensor system for detecting permittivity and permeability.

At times it may be advantageous to know the permittivity of the medium carrying the magnetic material. A sensor for detecting magnetic permeability and permittivity is shown in FIG. 31 where loops 2910 and capacitive plates 3110 are disposed normal to one another. In FIG. 32, the loops 2910 and capacitive plates 3110 are disposed on the same walls sides of the sensor volume 100.

With flow in the direction of the arrows 2920, the relative positions of the loops 2910 and plates 3110 in FIGS. 31 and 32, imply the magnetic properties (permeability) are first measured and then the dielectric properties (permittivity) are measured as the measured material is transported through the sensor volume 100. However, the plates 3110 and loops 2910 could be reversed in relative to the flow direction and measure the dielectric properties first and then the magnetic properties measured secondly.

With careful design, as is well known by those of ordinary skill in the art, the loops 2910 shown in FIG. 31 could be moved to be adjacent to the capacitive plates 3110 and have the magnetic and dielectric properties measured simultaneously. The present invention is not limited to any particular measurement order.

FIG. 33 shows an equivalent circuit 3300 diagram of the sensor volume 100.

Inductances, L1, L12, and L2 represent the sensor volume. Elements, C1, L3, and C3 represent components for matching the impedance of the sensor volume 100 to the appropriate value. Likewise, elements, C4, L4, and C2 represent components for matching the sensor volume 100 to the appropriate value. These values are such that, with a measurement alternating current source on the left and a load on the right, the circuit response will give the amplitude and phase response of the circuit as desired. In this case, L12 varies as a function of magnetic material fill in the sensor volume. Again, the circuit can be changed into a two-pole filter configuration with L12 representing the coupling between an input resonator and an output resonator.

FIG. 34 shows a representative phase curve for varying magnetic fill (L12 varying). The time-delay can then be empirically or theoretically related to the amount of magnetic fill in the sensor volume 100. As is known to those skilled in the art, measurements on the input port of the equivalent circuit 3300 may be used to indicate the value of L12 and thus magnetic fill in the sensor volume 100.

A typical curve of phase shift versus frequency for the circuit is shown in FIG. 34 where the left most curve results from a larger magnetic fill than that for the right most curve. This sensor shows a variation of a degree phase shift due to the quantity of magnetic fill. This results in a change in time-delay due to a change in phase shift at the same frequency.

Just as in the dielectric property case, the time-delay through the magnetic sensor volume 100 can be used to gauge the presence, and the relative amount of magnetic material in the sensor volume 100.

All the same applications and functionality shown in FIGS. 1, and 7a-20 pertains to the present inductive loop-type sensor volume 100 as well as the capacitive plate-type sensor volume 100.

Figure 35:
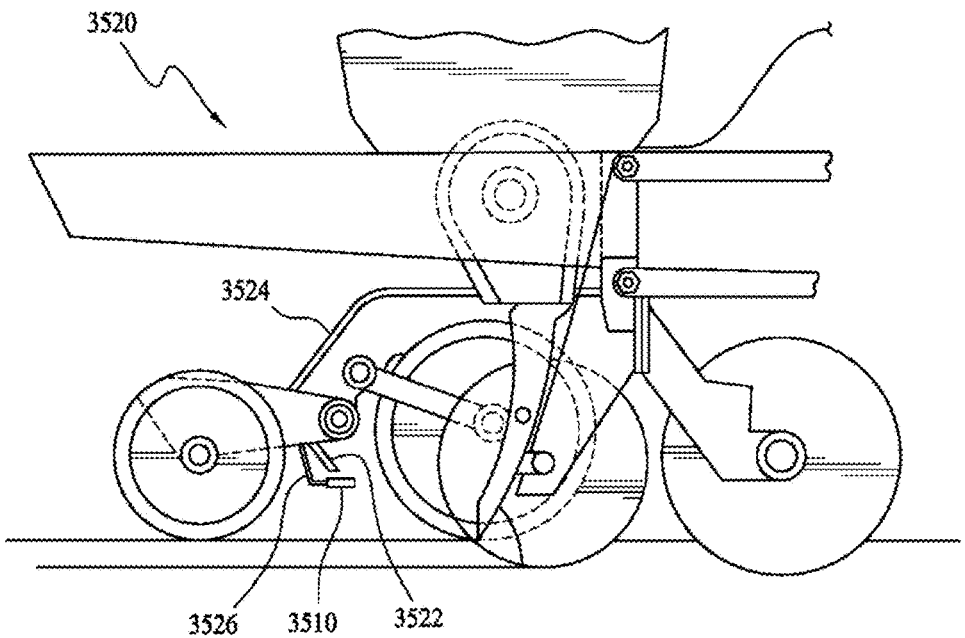
FIG. 35 is a perspective view, partially in cross-section, of another embodiment of the flow sensor apparatus which is detached from an application port of a planter row unit.

Referring now to FIG. 35, another embodiment of a flow sensor apparatus 3510 is illustrated on a corn planter row unit, designated generally as 3520. The flow sensor apparatus 3510 is positioned external to an application port 3522 of a supply tube, designated generally as 3524. The supply tube 3524 may be, for example, a liquid tube or granular tube. The detached flow sensor apparatus 3510 is mounted via a support bracket 3526 attached to the planter frame of the row unit 3520. The bracket may be attached to a side bolt or other part of the planter frame that the supply tube 3524 is attached to so that it is stationary with respect to the supply tube 3524. Although this embodiment has been illustrated relative to a corn planter row unit it may be used on other types of row units, or other application equipment.

Figure 36:
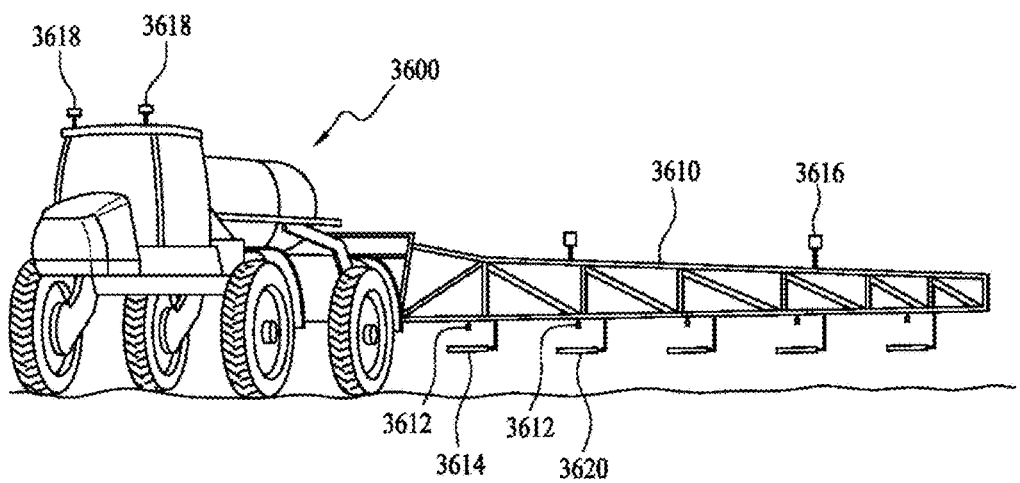
FIG. 36 is a perspective view of planter having a sprayer with a rear boom, and a detached flow sensor apparatus.

Referring now to FIG. 36 another type of application equipment in which the attached flow sensor apparatus may be utilized, is illustrated. FIG. 36 shows a self-propelled sprayer vehicle 3600 with a rear boom 3610.

Figure 37:
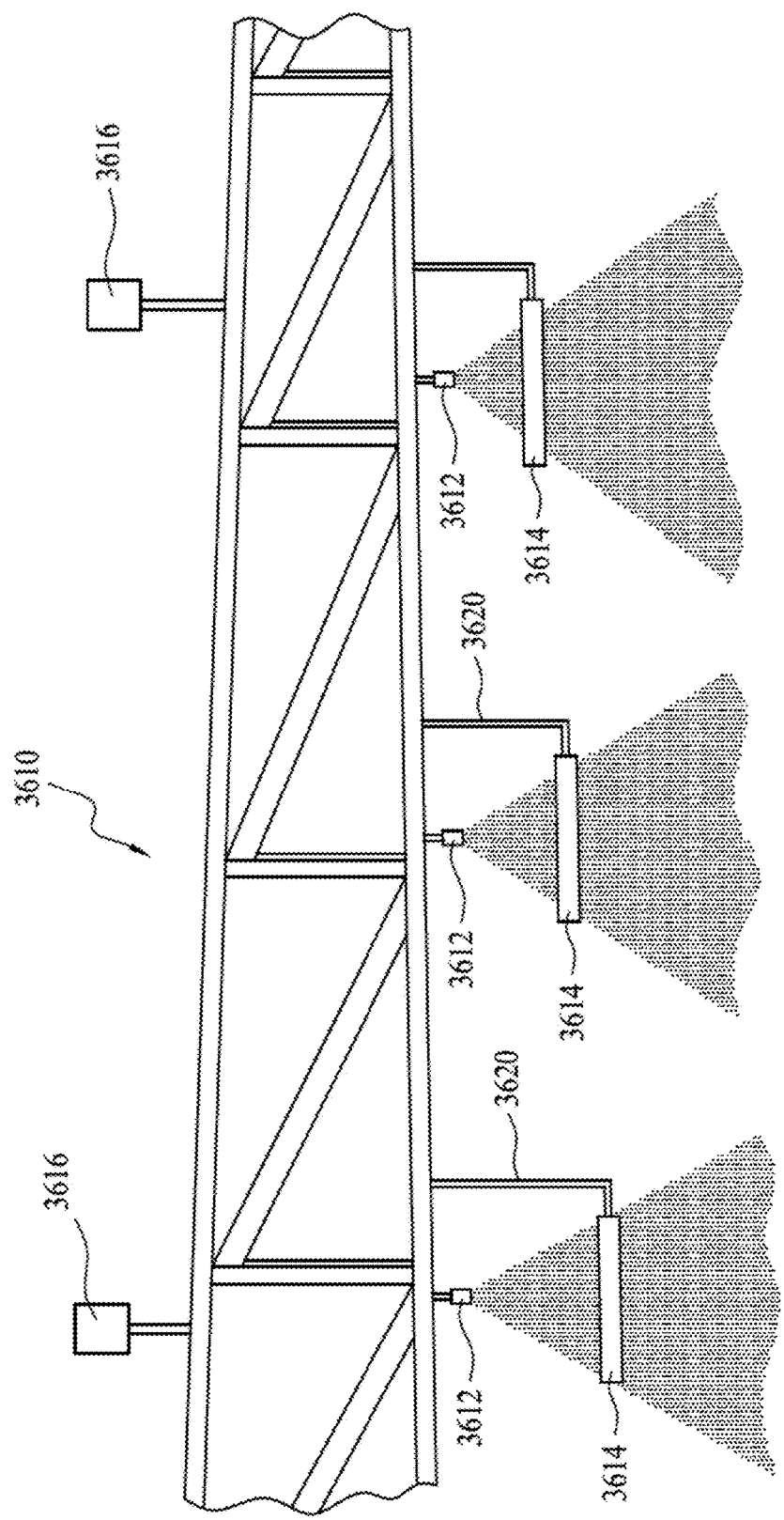
FIG. 37 is a schematic view of the sprayer boon with detached flow sensor apparatus and moisture sensors.

FIG. 37 shows an enlarged portion of a sprayer boom 3610 with nozzles (which may alternatively be referred to as discharge ports or application ports) 3612. The nozzles 3612 are operatively positioned relative to associated detached flow sensors 3614 that are configured to measure the volume of spray and pattern of the spray at a certain position below the application ports (i.e. nozzles) 3612. Preferably, above the boom, detached moisture sensors 3616 are positioned that measure the humidity (i.e. moisture content) of the air. Alternative mounting positions of the detached moisture sensors 3616 can be provided for mounting on the cab or other locations on the self-propelled spray vehicle 3600. Such alternate detached moisture sensors 3618 can be seen in FIG. 36. Suitable sprayer boom mounting brackets 3620 are utilized.

Figure 38:
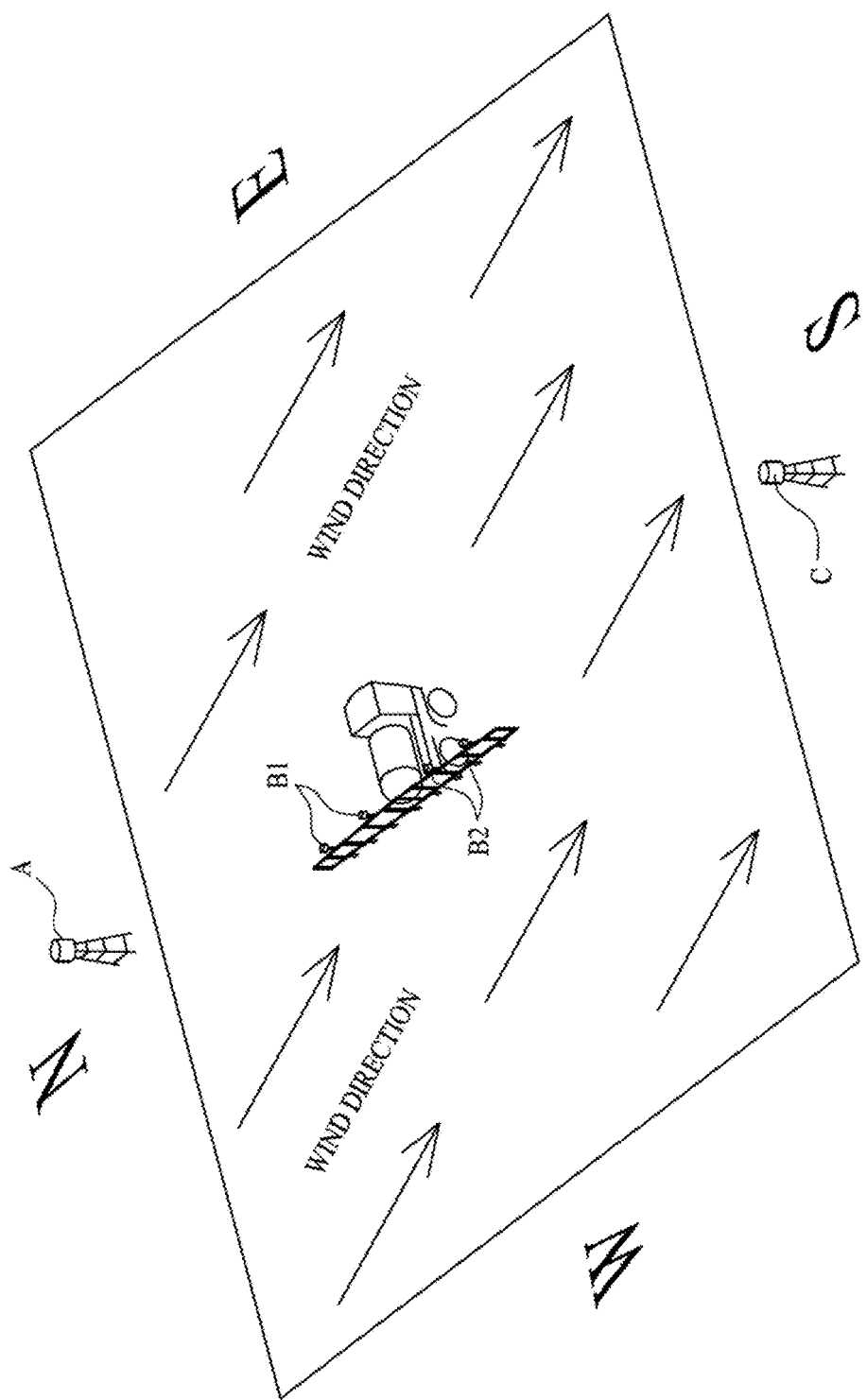
FIG. 38 is a schematic illustration of an agricultural product application system utilizing the detached flow sensors.

FIG. 38 is a schematic illustration of a field with indicated wind directions and sensors to determine movement of spray drift moving off the target area. FIG. 38 illustrates how to position sensors to monitor spray drift that flows off the target area or field being treated. Sensor A (i.e. upwind moisture/humidity sensor) is positioned upwind. Moisture/humidity sensors B1, B2, etc. can be mounted on the sprayer vehicle or the sprayer boom. The overall agricultural product application system, which may be the planter application or the spray application, can include a downwind moisture/humidity sensor C. The flow of the spray to the non-target area can be measured by comparing the readings of sensors A, B, and C. Depending on field conditions and wind conditions, the number and position of sensors can be varied for more accurate measurement of flow. The various flow sensor apparatus described above and below can be used in this agricultural product application system.

Figure 39:
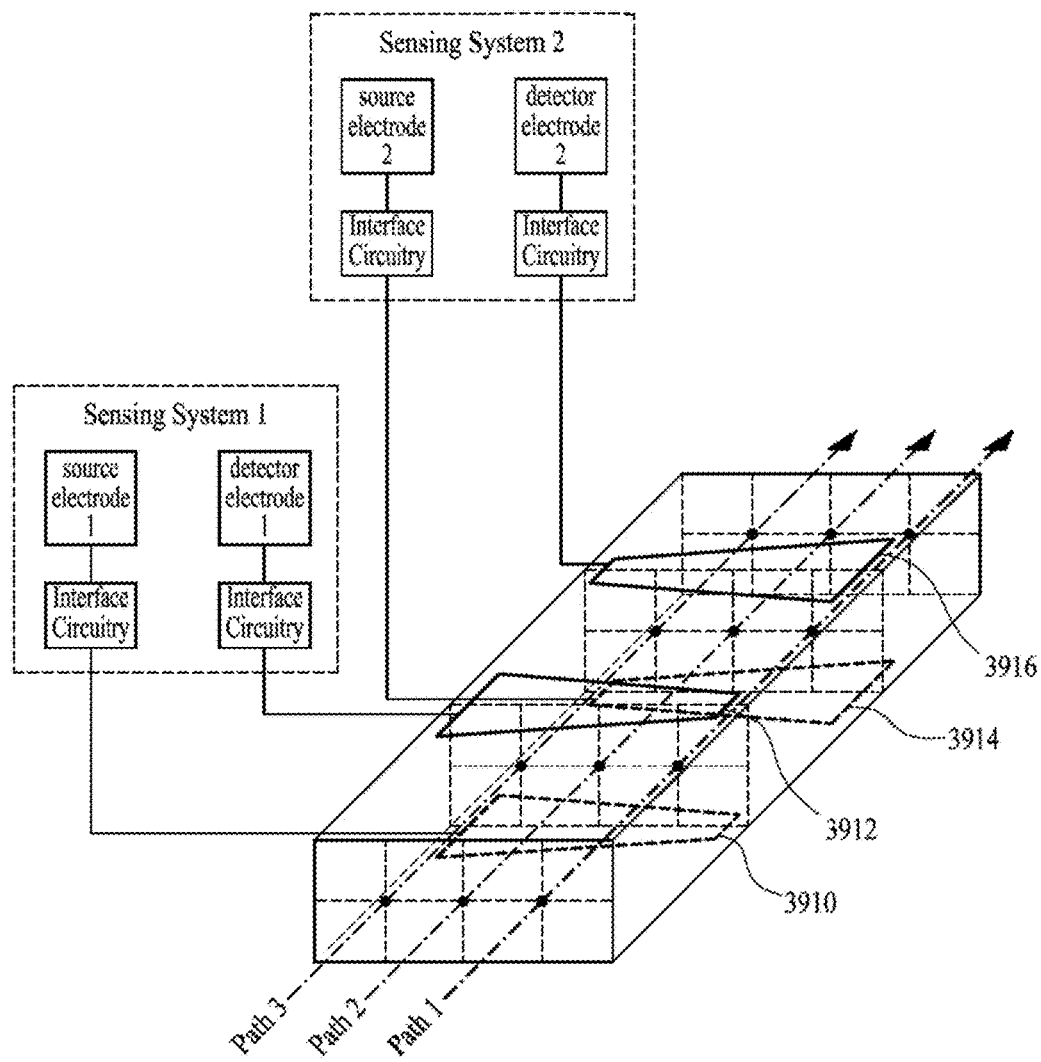
FIG. 39 is a perspective and phantom view of a detached double-sensor system using tapered electrodes for location sensing through the sensor.

FIG. 39 is a perspective and phantom view of a detached sensor system using tapered electrodes 3910, 3912, 3914, 3916 for location sensing through the sensor. The tapered electrodes have a different response which is used to determine the direction of material (i.e. contents) flowing through the sensor. If the material passes the wider part of the source electrode 1 it produces a signal which is detected by the detector electrode 1. As the material passes the narrower part of the source electrode 2 it produces another signal that is detected by detector electrode 2. Comparing the amplitude of the two signals the position of the material in the sensor body can be determined, and thus the path which the material takes through the sensor body. The sensor body includes any physical housing, the electrodes, and suitable circuitry which allows attachment of the detached sensor system to the various equipment. Thus, as in previous embodiments, this method involves bounding a volume by surfaces comprising a first electrically conductive plate, a second electrically conductive plate, not in physical contact with the first electrically conductive plate, and at least two sides made of electrically insulative material also bounding the volume. The source electrodes, in one preferred embodiment, emit an alternating-current. The detector electrodes and interface circuitry are reactive circuit elements. The material flowing through the sensor creates a change in the reactance in the circuitry.

The pairs of electrodes facilitate determining the path that material takes through the volume between the pairs of electrodes. The response, amplitude or phase, of the sensing systems connected between the first pair of electrodes (i.e. spaced-apart plates) 3910, 3912 and the second pair of electrodes 3914, 3916 in conjunction with determining the time of passage of material between the electrodes facilitates determining whether the material passes to one side, the middle, or the other side of the volume. Assuming material passing into the front and out of the rear of the sensor as depicted in FIG. 39, and when the path the material takes is to the left of the volume (i.e. Path 3), the sensing system response will be apparent for a longer period between the first pair of electrodes 3910, 3912 than the sensing system response that is apparent from the second pair of electrodes 3914, 3916. When the path the material takes is down the middle of the volume (i.e. Path 2), the responses of the two sensing systems will be substantially equal in time duration. In addition, if the amplitude responses of the sensing systems for each of the two pairs of electrodes are substantially equal, the sensing system amplitude response from the first pair of electrodes versus the sensing system amplitude response from the second pair of electrodes is indicative of the path taken by the material. When the path is to the left, the sensing system's amplitude response for the first pair of electrode will be higher than the sensing system's amplitude response for the second pair of electrodes. When the material takes a path down the middle of the volume, the amplitude responses for each pair of electrodes will be substantially equal. When the path is to the right (i.e. Path 1), the sensing system's amplitude response for the first pair of electrode will be lower than the sensing system's amplitude response for the second pair of electrodes. When used in a comparison detection system, the absolute magnitude of response from each pair of electrodes is not needed to determine the position of material passage. By comparing the amplitude responses from the two sensing systems in a relative magnitude manner, the path the material takes can be determined.

Position source electrodes and detector electrodes 3910, 3912, 3914, 3916 such as shown in FIG. 39 and specific for planter tube applications, in one preferred sensor embodiment has a width of approximately 1.5 inches and a height of ⅝ inches. In one preferred embodiment, they are placed such that seeds or granules travel pass through the volumes over which the tapered electrodes are nominally 1.75 inches center line to center line distance apart in the direction of travel. Position sensors for typical liquid based applicators may be of a larger size and of a different aspect ratio. The maximum size is limited such that at the frequency used for the sensing systems, the electromagnetic fields established in the sensor volume remain evanescent and not propagating external to the sensor as is well known to those skilled in the art.

Refractive index is the square root of relative dielectric constant. Incorporating sensors responsive to refractive index variation of specific chemical species into the apparatus of sensors 3614 facilitates tracking and placement determination of specific chemicals such as herbicides, insecticides, etc. In one preferred embodiment, a miniature sensor such as described in "Patterning of nanophotonic structures at optical fiber tip for refractive index sensing," Shawana Tabassum, Yifei Wang, Jikang Qu, Qiugu Wang, Seval Oren, Robert J. Weber, Meng Lu, Ratnesh Kumar, Liang Dong, SENSORS 2016, Caribe Royale All-Suite Hotel and Convention Center, Orlando, Fla., Oct. 30-Nov. 2, 2016, can be easily incorporated into the volume of sensors 3614. A multiplicity of such sensors facilitate determining not only amounts of chemicals passing through the volume but their position of application by judicially placing such sensors in the sensor 3614.

In some embodiments additional computation operations and resultant warning(s) may be utilized when the output of individual sensors of the multiplicity of sensors vary indicating no flow or limited flow when flow or full flow should be present.

The above embodiments are the preferred embodiments, but this invention is not limited thereto. It is, therefore, apparent that many modifications and variations of the present invention are possible in light of the above teachings. It is, therefore, to be understood that within the scope of the appended claims, the invention may be practiced otherwise than as specifically described.

What is claimed is:

1. A method of sensing the flow rate of a material comprising an agricultural product, the method comprising:
   (a) disposing two electrically conductive plates a predetermined distance apart;
   (b) incorporating a signal conditioning circuit, having an input and an output, with the two electrically conductive plates;
   (c) allowing matter to be present between said two electrically conductive plates;
   (d) measuring a time-delay with the matter from the input to the output of the signal conditioning circuit;
   (e) correlating the measured time-delay to an electrical capacity between the two electrically conductive plates; and
   (f) correlating a measured electrical capacity to the presence of the matter and amount of the matter between said spaced-apart plates,
   wherein said matter is directed to be present between said two electrically conductive plates by an application port at the end of a supply tube for the material to be measured, said two electrically conductive plates positioned external to and separate from said application port and thus positioned to provide measurement of the matter.

2. The method of claim 1 wherein measuring the electrical capacity comprises sensing a change in the electrical capacity.

3. The method of claim 1 wherein measuring the electrical capacity comprises sensing a signal related to an effective dielectric constant of a mass in the volume.

4. The method of claim 3 additionally comprising:
   (a) taking a first temporal derivative of the signal related to the effective dielectric constant of mass;
   (b) determining a zero-crossing of the first temporal derivative; and
   (c) calculating a time at which the zero-crossing occurs.

5. The method of claim 1 wherein correlating the electrical capacity measurement to the presence of the matter comprises empirically determining a correlation between a thermodynamic state of the material and the electrical capacity of the material.

6. The method of claim 1 wherein correlating the electrical capacity measurement to the presence of the matter comprises correlating a dielectric mass to a mass of the matter.

7. The method of claim 1 wherein a volume is bounded on two sides by the two electrically conducting plates and the matter is stationary relative to the volume.

8. The method of claim 1 wherein a volume is bounded on two sides by the two electrically conducting plates and the matter is moving relative to the volume.

9. The method of claim 1 wherein the matter between said spaced-apart plates comprises a sensing element and the presence of the matter comprises a location of the material.

10. The method of claim 9 wherein the sensing element comprises a shape selected from the group consisting of a bead, a cone, and a truncated cone.

11. The method of claim 9 wherein the location the sensing element changes as a function of flow rate.

12. The method of claim 9 wherein a dielectric constant of the sensing element is not equal to a dielectric constant of a flowing substance between the spaced-apart plates.

13. The method of claim 1 additionally comprising:
 (a) tapering the two electrically conductive plates in a transverse direction to matter flow; and
 (b) sensing a transverse location of the matter between the two tapered electrically conductive plates.

14. The method of claim 13 wherein sensing a transverse location comprises:
 (a) sensing a duration of a signal of the electrical capacity; and
 (b) correlating said duration to the transverse location of the matter between the two tapered electrically conductive plates.

15. The method of claim 13 wherein the two tapered electrically conductive plates comprise a first two tapered electrically conductive plates and the transverse location comprises a first-plane transverse location, that is, the transverse location in a first plane, the method further comprising:
 (a) tapering a second two electrically conductive plates in a transverse direction;
 (b) disposing the second two electrically conductive plates at an angle, not parallel, to the first electrically conductive plates; and
 (c) sensing a second-plane transverse location of the matter between the second two tapered electrically conductive plates.

16. An electronic method for measuring mass comprising:
 (a) bounding a volume by surfaces comprising a first electrically conductive plate, a second electrically conductive plate, not in physical contact with the first electrically conductive plate, and at least two sides made of electrically insulative material also bounding the volume;
 (b) incorporating a signal conditioning circuit; having an input and an output, with the two electrically conductive plates;
 (c) measuring the time-delay from the input to the output of the signal conditioning circuit;
 (d) correlating the measured circuit time-delay to the electrical capacity between the two electrically conductive plates;
 (e) measuring a dielectric mass of a contents of the volume; and
 (f) correlating said dielectric mass to a mass of the contents of the volume;
 wherein said mass of the contents is directed to be present between said two electrically conductive plates by an application port at the end of a supply tube for the contents to be measured, said contents comprising agricultural products, said two electrically conductive plates positioned external to and separate from said application port and thus positioned to provide measurement of the contents.

17. The method of claim 16 wherein said contents completely fills said volume.

18. The method of claim 16 wherein said contents only partially fills said volume.

19. The method of claim 16 additionally comprising:
 (a) producing a signal related to the dielectric mass;
 (b) passing said signal through a communication bus; and
 (c) receiving the signal by an operator interface from the communication bus.

20. The method of claim 19 additionally comprising:
 (a) comparing the signal to at least one tolerance value; and
 (b) indicating a warning by the operator interface when the signal fails to satisfy the at least one tolerance value.

21. The method of claim 20 additionally comprising adjusting the at least one tolerance value.

22. The method of claim 16 wherein the bounding volume comprises a first bounding volume and the dielectric mass comprises a first dielectric mass, the method additionally comprising:
 (a) bounding a second volume by surfaces comprising a third electrically conductive plate, a fourth electrically conductive plate, not in physical contact with the third electrically conductive plate, and at least two sides made of electrically insulative material also bounding the volume;
 (b) incorporating an additional signal conditioning circuit, having an input and an output, with the third and fourth electrically conductive plates;
 (c) measuring a time-delay from the input to the output of the additional signal conditioning circuit;
 (d) correlating the measured circuit time-delay of the additional signal conditioning circuit to the electrical capacity between the third and fourth electrically conductive plates;
 (e) measuring at least a second dielectric mass of a contents of the second volume; and
 (f) correlating said second dielectric mass to a second mass of the contents of the second volume.

23. The method of claim 22 additionally comprising determining a mass flow rate based on the measured first mass of the contents of the first volume and the second mass of the contents of the second volume.

24. The method of claim 23 additionally comprising:
 (a) correlating the mass flow rate to a pulse frequency; and
 (b) sending the pulse frequency to a monitoring system.

25. The method of claim 16 additionally comprising exciting the first and second electrically conductive plates with a predetermined frequency.

26. The method of claim 25 wherein the frequency is chosen from a range of frequencies, said range of frequencies is radio frequencies.

27. A flow sensor apparatus for monitoring a directed stream of an agricultural product from an application port at the end of a supply tube, said directed stream having a target directed portion and an off-target portion, said flow sensor apparatus comprising:
 (a) a first electrically conductive plate;
 (b) a second electrically conductive plate disposed a distance away from the first electrically conductive plate;
 (c) a first electrically nonconductive surface disposed to connect edges of the first and second electrically conductive plates;
 (d) a second electrically nonconductive surface disposed to form a volume, said volume bounded by surfaces comprising the first electrically conductive plate, the second electrically conductive plate, the first electrically nonconductive surface, and the second electrically non-conductive surface;

(e) a signal conditioning circuit, having an input and an output, with the first and second electrically conductive plates;
(f) means for measuring the circuit time-delay from the input to the output of the signal conditioning circuit;
(g) means for correlating the measured circuit time-delay to the electrical capacity between the two electrically conductive plates;
(h) a dielectric constant determining circuit to determine an effective dielectric constant between the first and second electrically conductive plates; and
(i) a computational function to correlate the effective dielectric constant to a presence of material inside the volume,
wherein said first electrically conductive plate, said second electrically conductive plate, said first electrically nonconductive surface, and said second electrically nonconductive surface are positioned external to and separate from said application port and thus positioned to provide measurement of the agricultural product.

28. The apparatus of claim 27 wherein the computational function correlates the effective dielectric constant to a mass of the material inside the volume.

29. The apparatus of claim 27 wherein the computational function correlates the effective dielectric constant to a location of the material inside the volume.

30. The apparatus of claim 27 wherein the volume comprises a flow measurement device, said flow measurement device comprising a movable mass, a location of said movable mass indicating a flow rate.

31. The apparatus of claim 27 additionally comprising:
(a) a communication bus to carry a signal related to the dielectric constant; and
(b) a monitor to which the communication bus is connected and that provides an operator interface to the signal conditioning circuit.

32. The apparatus of claim 31 wherein the monitor is an agricultural implement monitor.

33. The apparatus of claim 31 wherein the monitor is a seed sensor unit.

34. The apparatus of claim 33 additionally comprising a sensing unit for sensing pulses as a function of mass flow rate.

35. The apparatus of claim 33 wherein the signal related to the dielectric constant is compatible with the seed sensor unit.

36. A method of sensing the flow rate of a material comprising an agricultural product, the method comprising:
(a) disposing two inductive loops a predetermined distance apart;
(b) incorporating a signal conditioning circuit, having an input and an output, with the two inductive loops by measuring a signal time-delay from a first of the two inductive loops to a second of the two inductive loops;
(c) measuring the time-delay from the input to the output of the signal conditioning circuit;
(d) allowing some matter to be present between said two inductive loops;
(e) correlating the measured time-delay to a measured magnetic permeability of matter between the two inductive loops; and
(f) correlating the measured magnetic permeability to the presence of the matter between said two inductive loops
wherein said matter is directed to be present between said two electrically conductive plates by an application port at the end of a supply tube for the material to be measured, said two electrically conductive plates positioned external to and separate from said application port and thus positioned to provide measurement of the matter.

37. The method of claim 36 wherein at least one of the two inductive loops comprises a plate.

38. The method of claim 36 additionally comprising:
(a) disposing two electrically conductive plates a predetermined distance apart;
(b) allowing the matter to be present between said two electrically conductive plates;
(c) incorporating a signal conditioning circuit, having an input and an output, with the two electrically conductive plates;
(d) measuring a time-delay with the matter from the input to the output of the signal conditioning circuit;
(e) correlating the measured circuit time-delay to the electrical capacity between the two electrically conductive plates; and
(f) correlating the measured electrical capacity to the presence and amount of the matter between said spaced-apart plates.

39. The method of claim 38 wherein measuring the magnetic permeability comprises sensing an electrical signal related to a mass in the volume.

40. The method of claim 39 additionally comprising:
(a) taking a first temporal derivative of the signal related to the mass;
(b) determining a zero-crossing of the first temporal derivative; and
(c) calculating a time at which the zero-crossing occurs.

41. The method of claim 40 wherein correlating the magnetic permeability measurement to the presence of the matter comprises empirically determining a correlation between a thermodynamic state of the material and the magnetic permeability of the material.

42. An apparatus, comprising:
(a) a first inductive loop;
(b) a second inductive loop disposed a distance away from the first inductive loop;
(c) a signal conditioning circuit, having an input and an output, incorporated with the first and second inductive loops;
(d) means for measuring a time-delay from the input to the output of the signal conditioning circuit;
(e) means for correlating the measured circuit time-delay to the effective magnetic permeability of matter between the first and second inductive loops;
(f) a volume comprising at least one surface, said first and second inductive loops being disposed on the at least one surface; and
(g) a computational function to correlate the effective magnetic permeability to a presence of said material inside the volume,
wherein said matter is directed to be present between said first and said second inductive loops by an application port for the material to be measured, said two electrically conductive plates positioned external to and separate from said application port and thus positioned to provide measurement of the matter.

43. The apparatus of claim 42 wherein the computational function correlates the effective magnetic permeability to a mass of the material inside the volume.

44. The apparatus of claim 42 additionally comprising:
(a) a communication bus to carry a signal related to the magnetic permeability; and (b) a monitor to which the communication bus is connected and that provides an operator interface to the circuit.

45. The apparatus of claim 42 additionally comprising a sensing unit for sensing pulses as a function of mass flow rate.

46. The method of claim 1 additionally comprising:
(a) disposing two inductive loops a predetermined distance apart;
(b) incorporating a signal conditioning circuit, having an input and an output, with the two inductive loops;
(c) measuring a time-delay from the input to the output of the signal conditioning circuit;
(d) allowing some matter to be present between said two inductive loops;
(e) correlating the measured circuit time-delay to the magnetic permeability of the matter between the two inductive loops; and
(f) correlating the measured magnetic permeability to the presence of the matter between said two inductive loops.

47. The method of claim 1 wherein the material is a mixture of different materials that vary with time.

48. The method of claim 1 wherein the material is a mixture of different materials that vary with time and flows of these mixtures vary with time.

49. A method of sensing the flow rate of a material comprising an agricultural product, the method comprising:
(a) disposing two electrically conductive plates a predetermined distance apart;
(b) incorporating a signal conditioning circuit, having an input and an output, with said two electrically conductive plates;
(c) incorporating an alternating-current source and reactive circuit elements with the first of the two electrically conductive plates;
(d) incorporating a load and reactive circuit elements with said second of the two electrically conductive plates;
(e) allowing some matter to be present between said two electrically conductive plates;
(f) measuring a time-delay with the matter from the source to the load of the signal conditioning circuit; and
(g) correlating the measured time-delay to the presence of the matter between said spaced-apart plates,
wherein said matter is directed to be present between said two electrically conductive plates by an application port at the end of a supply tube for the material to be measured, said two electrically conductive plates positioned external to and separate from said application port and thus positioned to provide measurement of the matter.

50. An agricultural product application system, comprising:
a movable application equipment, comprising a flow sensor apparatus for monitoring a directed stream of agricultural products from an application port at the end of a supply tube, said directed stream having a target directed portion and an off-target portion, said flow sensor apparatus comprising:
(a) a first electrically conductive plate;
(b) a second electrically conductive plate disposed a distance away from the first electrically conductive plate;
(c) a first electrically nonconductive surface disposed to connect edges of the first and second electrically conductive plates;
(d) a second electrically nonconductive surface disposed to form a volume, said volume bounded by surfaces comprising the first electrically conductive plate, the second electrically conductive plate, the first electrically nonconductive surface, and the second electrically non-conductive surface;
(e) a signal conditioning circuit, having an input and an output, with the first and second electrically conductive plates;
(f) means for measuring the time-delay from the input to the output of the signal conditioning circuit;
(g) means for correlating the measured time-delay to the electrical capacity between the two electrically conductive plates;
(h) a dielectric constant determining circuit to determine an effective dielectric constant between the first and second electrically conductive plates; and
(i) a computational function to correlate the effective dielectric constant to a presence of material inside the volume,
wherein said first electrically conductive plate, said second electrically conductive plate, said first electrically nonconductive surface, and said second electrically nonconductive surface are positioned external to and separate from said application port;
at least one upwind moisture/humidity sensor positioned upwind of said movable application equipment; and,
at least one downwind moisture/humidity sensor positioned downwind of said movable application equipment.

* * * * *